(12) United States Patent
Thiagarajan

(10) Patent No.: US 7,611,471 B2
(45) Date of Patent: Nov. 3, 2009

(54) HEART DIAGNOSIS SYSTEM

(75) Inventor: Arvind Thiagarajan, Chennai (IN)

(73) Assignee: HD Medical Inc., Portland, OR (US)

( * ) Notice: Subject to any disclaimer, the term of this patent is extended or adjusted under 35 U.S.C. 154(b) by 276 days.

(21) Appl. No.: 10/477,606

(22) PCT Filed: May 28, 2002

(86) PCT No.: PCT/SG02/00106

§ 371 (c)(1), (2), (4) Date: Nov. 14, 2003

(87) PCT Pub. No.: WO02/096293

PCT Pub. Date: Dec. 5, 2002

(65) Prior Publication Data

US 2004/0138572 A1    Jul. 15, 2004

(30) Foreign Application Priority Data

May 28, 2001   (IN)   .................. 431/MAS/2001

(51) Int. Cl.
*A61B 5/02* (2006.01)
(52) U.S. Cl. .................................. 600/528
(58) Field of Classification Search ............ 600/509, 600/508, 514, 528; 607/17, 18
See application file for complete search history.

(56) References Cited

U.S. PATENT DOCUMENTS

| | | | |
|---|---|---|---|
| 3,878,832 A * | 4/1975 | Tickner et al. ............ 600/508 |
| 5,119,432 A * | 6/1992 | Hirsch ..................... 324/76.19 |
| 5,923,780 A | 7/1999 | Morfill et al. |
| 6,048,319 A * | 4/2000 | Hudgins et al. ............ 600/528 |
| 6,898,459 B2 * | 5/2005 | Hayek et al. ............... 600/509 |
| 2002/0052559 A1 * | 5/2002 | Watrous .................... 600/528 |
| 2002/0151812 A1 * | 10/2002 | Scheiner et al. ............ 600/528 |
| 2003/0009108 A1 * | 1/2003 | Kawaguchi ................. 600/528 |

FOREIGN PATENT DOCUMENTS

| WO | WO 92/09046 | 5/1992 |
|---|---|---|
| WO | WO 01/62152 AL | 8/2001 |

OTHER PUBLICATIONS

H. Liang, S. Lukkarinen, I Hartimo, "Heart Sound Segmentation Algorithm Based on Heat Sound Envelogram", Computers in Cardiology '97, Lund, Sweden, Sep. 1997. pp. 105-108.

* cited by examiner

*Primary Examiner*—Angela D Sykes
*Assistant Examiner*—Michael Kahelin
(74) *Attorney, Agent, or Firm*—Lawrence Y.D. Ho & Associates; Kang Lim

(57) ABSTRACT

The invention provides a method and apparatus for analysing a heart signal from a beating heart, the method comprising: collecting the heart signal, performing a cluster analysis of the signal to identify the first heart sound and the second heart sound, determining an energy envelope for each of a plurality of regions in the signal, determining the area of each of the energy envelopes, and classifying features in the signal by an analysis incorporating at least the areas, whereby one or more characteristics of the heart can be determined.

24 Claims, 28 Drawing Sheets

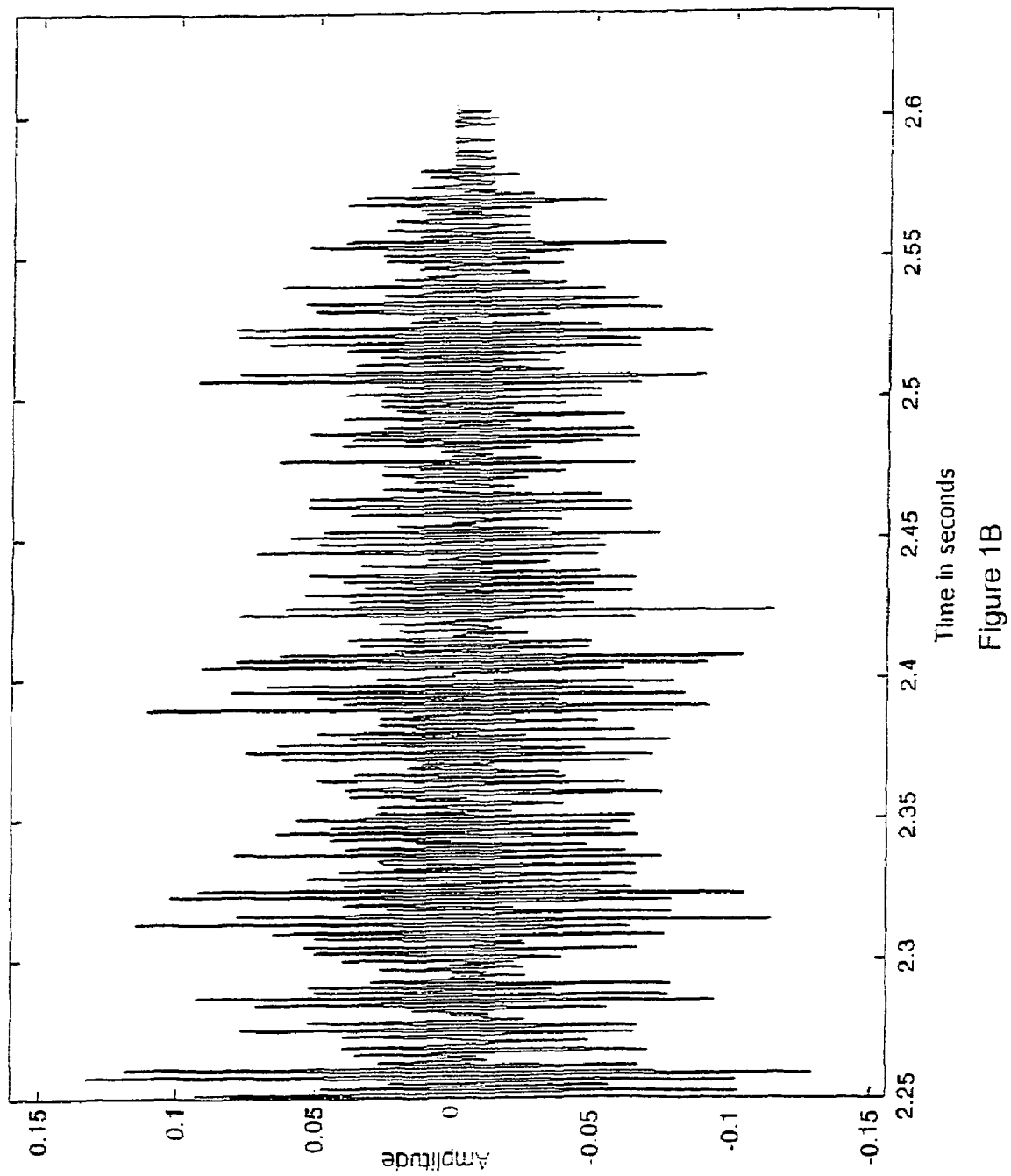

HEART DIAGNOSIS SYSTEM

FIELD OF THE INVENTION

The present invention relates to a method and apparatus for diagnosing heart conditions.

BACKGROUND OF THE INVENTION

The heart sounds are relatively brief, discrete auditory vibrations that can be characterised by the intensity (loudness), frequency (pitch), and quality (timbre). The S1 identifies the onset of ventricular systole, and S2 identifies the onset of diastole. These two auscultatory events establish a framework within which other heart sounds and murmurs can be placed and timed. The basic heart sounds are the S1, S2, S3, and S4. Each of these events can be normal or abnormal.

First heart sound (S1) occurs early in ventricular systole. S1 consists of two components. The first major component is associated with closure of the mitral valve and coincides with abrupt arrest of leaflet motion when the cusps reach their fully closed positions.

The origin of the second component is generally assigned to the closure of the tricuspid valve. Because the intensity of S1 depends on the velocity of blood and resultant force of closure of the AV valves, factors that increase the force and velocity of ventricular pressure rise tend to increase the intensity of S1. The position of the AV valves at the onset of systole also affects S1 intensity. If ventricular contraction occurs against a wide open valve, the LV leaflets attain a higher velocity (thus louder S1) than if the valve were partially closed. Second heart sound (S2).

The second heart sound occurs at the end of systole. S2, like S1, has two components. The first component of the second heart sound is designated 'aortic' (A2) and the second 'pulmonic' (P2).

Since systole (the time of ventricular contraction) is usually shorter than diastole (the time of ventricular relaxation) there is a longer pause between S2 and S1 than between S1 and S2.

S1 is of longer duration and of lower pitch; S2 is of shorter duration and of higher pitch. S1 is usually best heard at the apex; S2 is usually best appreciated in the aortic and pulmonic areas.

The presence of tachycardia or bradycardia may change the above relationships.

The physiologic third heart sound (S3) is a low-pitched vibration occurring in early diastole during the time of rapid ventricular filling. The sound of an S3 is produced by the abrupt transmission of forces to the chest wall when the blood mass enters the right ventricle. An S3 is commonly heard in children and adolescents and in some young adults. When heard after the age of 30, it is called a gallop sound and is a sign of pathology, such as left ventricular failure. The physiologic S3 occurs just after A2 and is best heard at the apex with a patient in the left semilateral position. S3 normally disappears completely when the patient sits or stands or performs any manoeuver that lowers heart rate. Conversely, factors that increase heart rate, such as exercise, tend to accentuate a physiologic S3.

The physiologic fourth heart sound (S4) is a very soft, low-pitched noise occurring in late diastole, just before S1. S4 generation is related to the ventricular filling by atrial systole. Vigorous atrial contraction produces rapid acceleration of blood mass. Associated with this event are vibrations in the left ventricle wall and mitral apparatus which are heard as the S4.

A physiologic S4 may be heard in infants, small children, and adults over the age of 50. It is usually heard only at the apex with the patient placed in the left semilateral position. A physiologic S4 is poorly transmitted and is rarely accompanied by a shock (when the S4 can be felt as well as heard). Wide transmission of a loud S4 associated with a shock is pathologic and is referred to as an S4 gallop.

As in the case of S3, manoeuvers that increase the force and frequency of ventricular contraction will accentuate S4. Conversely, manoeuvers associated with cardiac slowing will diminish S4 intensity.

Aortic ejection clicks are high pitched sounds that occur in early systole. There are no associated accentuating manoeuvers. Intensity is not affected by respiration or patient position. Left sided valvular ejection sounds are heard best in the aortic area, and are not widely transmitted. The ejection click of aortic stenosis is heard best in the mitral area, but is widely transmitted. Aortic ejection clicks are seen in congenital and rheumatic valvular aortic stenosis with a deformed but flexible aortic valve.

Conditions associated with obstruction of the aorta, such as systemic hypertension and coarctation of the aorta, are also associated with aortic ejection clicks.

Pulmonic ejection clicks, like aortic ejection clicks, are high pitched sounds of early systole. Unlike the aortic click, the pulmonic ejection click is heard best in the pulmonic area and is rarely transmitted. The pulmonic ejection click is the only right heart sound that decreases in intensity during inspiration. Pulmonic ejection clicks are often associated with mild to moderate valvular pulmonic stenosis, dilation of the pulmonary artery (as seen in pulmonary hypertension), and tetralogy of Fallot.

Non-ejection clicks are high frequency sounds of mid- to late-systole. Clicks associated with tricuspid valve prolapse ("tricuspid clicks") are best appreciated along the left lower sternal border. Mitral and tricuspid clicks are sometimes only heard with the patient standing. In this position, the ventricles are smaller and the degree of prolapse of both mitral and tricuspid valves is increased. Having the patient exercise or move to a position other than standing usually diminishes the intensity of both mitral and tricuspid clicks. Inspiration tends to increase the intensity of the tricuspid click.

Mitral clicks, commonly associated with mitral valve prolapse, are heard best in the mitral area and usually are not widely transmitted. Mitral clicks are sometimes only heard with the patient standing. In this position, the ventricles are smaller and the degree of prolapse of the mitral valves is increased. Having the patient exercise or move to a position other than standing usually diminishes the intensity of the clicks.

The opening snap of the mitral valve is heard best midway between the pulmonic and mitral areas. The mitral valve opening snap has a quality similar to the normal heart sounds and is often confused with a splitting S2. The brief, sharp, rather snapping sound is heard shortly after the A2 component of S2. When loud, it is widely transmitted over the entire precordium. Optimum audibility is often achieved by turning the patient to the left lateral position. Standing tends to lower the left atrial pressure and thus increase the A2-OS interval. A soft OS may be intensified after exercise that increases atrial pressure. The A2-OS interval is not altered during different phases of respiration; however, the Mitral Valve Opening Snap is usually loudest on expiration.

The auscultatory characteristics of the Tricuspid Valve Opening Snap resemble those of the Mitral Valve Opening Snap. However, the Tricuspid Valve Opening Snap is louder at the Left Lower Sternal Border or over the xiphoid area.

Additionally, the loudness of the Tricuspid Valve Opening Snap usually increases markedly during inspiration, whereas the Mitral Valve Opening Snap is often louder on expiration. The interval between the first component of S2 (A2) and the Tricuspid Valve Opening Snap tends to be longer than the interval between A2 and the Mitral Valve Opening Snap. Sitting up tends to accentuate the Tricuspid Valve Opening Snap.

The site of maximum intensity of a sound or murmur is useful but does not always decide its origin. The direction of selective spread and the effect of respiration are also useful factors to take into account.

i) Mitral valve sounds and murmurs are loudest at the apex (MA), with the patient turned on to the left side;

ii) Tricuspid valve sounds and murmurs are localized to the lower left sternal edge (TA), but spread to the apex if the right ventricle is dilated and the left ventricle rotated posteriorly, e.g. Atrial Septal Defect (ASD);

iii) Aortic valve sounds and murmurs: ejection murmurs are loudest in the aortic area (AA, second right interspace) and at the cardiac apex, and are often transmitted to the carotid arteries in the neck, but a short murmur confined to the neck may be heard in young normal subjects with a big stroke volume; in older subjects it suggests carotid stenosis; regurgitant early diastolic murmurs are usually loudest in the third and fourth left intercoastal spaces at the left sternal edge with the patient leaning forward in expiration; with aortic dilation, however, the murmur is usually maximal in the aortic area;

iv) Pulmonary valve sounds and murmurs are loudest in the pulmonary area (PA, third left interspace) but often heard lower; and v) Murmurs over the back: the systolic murmurs of peripheral pulmonary stenosis and coarctation of the aorta are heard maximally over the back; a continuous murmur suggests a communication between the descending aorta and pulmonary circulation.

Heart Murmurs have the following types:

1) Innocent Murmurs are associated with no known abnormality either structural or physiological.

2) Physiological Murmurs are caused by disturbance in the physiology of the circulation, e.g., those related to hyperkinetic state or overactive circulation, excitement, anaemia, fever thyrotoxicosis, pregnancy, cor pulmonale, portal hypertension or beri beri heart disease.

3) Relative or Functional Murmurs are caused by structural disorders not involving valves or abnormal cardiac or vascular communications; murmurs caused by dilation of heart chambers or dilation of vessels.

4) Organic Murmurs are caused by valvular disease, shunts or narrowed vessels.

A widely used existing device is the stethoscope, by means of which little more than the speed of the heartbeat can be observed. The mechanical working of the heart involves complexity that produces, for example, heart sounds and murmurs, which the doctor must detect and characterise (in terms of, for example, location and timing) if an effective diagnosis is to be made.

Electrocardiograms, on the other hand, provide information on the electrical characteristics of the heart, and not mechanical or structural abnormalities. To analyze and detect such mechanical and structural defects, a 2-D ultrasound echocardiogram machine is required. However, although currently one of the most advanced pieces of equipment for detecting cardiac defects, its cost is typically several thousands of dollars (US). Consequently, such echocardiogram machines are generally available only in sophisticated diagnostic labs or larger hospitals, and thus beyond the means of an ordinary cardiologist or general physician. Further, the complexity of echocardiogram machines is such that well-trained lab technicians are required for their operation.

Without herein suggesting that it forms a part of the common general knowledge, WO 01/62152 discloses a system for analysing heart sounds, in which the sounds are filtered and parsed into a sequence of individual heart cycles. Systolic and sub-systolic intervals are identified, and energy values computed for comparison with threshold levels. However, this document teaches the use only of either wavelet transform analysis or Fourier transform analysis in order to identify individual peaks and hence the systole and diastole, and does not take the energy envelope of the heart signal into account.

SUMMARY OF THE INVENTION

In a first broad aspect, therefore, the present invention provides a method of analysing a heart signal from a beating heart comprising:

collecting said heart signal;

performing a cluster analysis of said signal to identify the first heart sound and the second heart sound;

determining an energy envelope for each of a plurality of regions in said signal;

determining the area of each of said energy envelopes; and classifying features in said signal by an analysis incorporating at least said areas;

whereby one or more characteristics of said heart can be determined.

Thus, by means of cluster analysis, the heart sounds can be extracted (particularly into systolic and diastolic intervals) without external timing reference. The various features of the heart sounds are then analyzed and classified.

Preferably said method includes comparing one or more of said areas with at least one other of said areas. More preferably said method includes determining one or more ratios, each comprising the ratio of one of said areas and another of said areas, and comparing said ratios with respective predetermined threshold values for said ratios, and thereby determining one or more characteristics of said heart.

The method may, in one embodiment, include comparing one or more of said areas with respective predetermined threshold values for said areas, and thereby determining one or more characteristics of said heart.

Preferably said method includes smoothing each of said energy envelopes.

Preferably each of said energy envelopes is a Shannon's energy envelope.

In one embodiment, said method includes determining the energy envelope for the systolic region and for the diastolic region.

Preferably said method includes determining the energy envelope for a plurality of regions within each of the systolic and diastolic regions, and more preferably determining the energy envelope for three regions within the systolic region and for three regions within the diastolic region.

Preferably said signal is a sound signal. However, said signal could be any other suitable signal, such as an electric signal. The method will generally include converting said signal to an electric signal and possibly to a digital electric signal.

Preferably the method includes prompting a user for user input if unable to form a diagnosis, said user input including a user interpretation of said heart signal.

In a second broad aspect, the present invention provides a method of analysing a physiological signal comprising:
  collecting said signal;
  performing a cluster analysis of said signal to identify one or more features;
  determining an energy envelope for each of a plurality of regions defined by one or more of said features;
  determining the area of each of said energy envelopes; and
  classifying features in said signal by an analysis incorporating at least said areas;
  determining one or more physiological characteristics from said signal.

In a third broad aspect, the present invention provides an apparatus for analysing a heart signal from a beating heart comprising:
  a detector for collecting said heart signal;
  data processing means for:
    receiving said heart signal,
    performing a cluster analysis of said signal to identify the first heart sound and the second heart sound,
    determining an energy envelope for each of a plurality of regions in said signal,
    determining the area of each of said energy envelopes, and
    forming a classification of each of one or more features in said signal by an analysis incorporating at least said areas; and
  data output means for displaying said classification;
  whereby one or more characteristics of said heart can be determined.

Preferably said data processing means is operable to compare one or more of said areas with at least one other of said areas. More preferably said data processing means is operable to determine one or more ratios, each comprising the ratio of one of said areas and another of said areas, and to compare said ratios with respective predetermined threshold values for said ratios, and thereby determine one or more characteristics of said heart.

The data processing means may, in one embodiment, be operable to compare one or more of said areas with respective predetermined threshold values for said areas, and thereby determining one or more characteristics of said heart.

Preferably said data processing means is operable to smooth each of said energy envelopes.

Preferably each of said energy envelopes is a Shannon's energy envelope.

In one embodiment, said data processing means is operable to determine the energy envelope for the systolic region and for the diastolic region.

Preferably said data processing means is operable to determine the energy envelope for a plurality of regions within each of the systolic and diastolic regions, and more preferably to determine the energy envelope for three regions within the systolic region and for three regions within the diastolic region.

Preferably said signal is a sound signal.

The apparatus will generally include a converter for converting said signal to an electric signal and possibly to a digital electric signal.

Preferably the data processing means includes means for prompting a user for user input and for receiving user input, and is operable to prompt said user for user input if unable to form a diagnosis, said user input including a user interpretation of said heart signal.

The present invention also provides an apparatus for analysing a physiological signal comprising:
  a detector for collecting said signal;
  data processing means for:
    receiving said signal,
    performing a cluster analysis of said signal to identify one or more features,
    determining an energy envelope for each of a plurality of regions defined by one or more of said features,
    determining the area of each of said energy envelopes, and
    forming a classification of each of one or more features in said signal by an analysis incorporating at least said areas; and
  data output means for displaying said classification;
  whereby one or more physiological characteristics can be determined.

BRIEF DESCRIPTION OF THE FIGURES

In order that the present invention may be more clearly ascertained, a preferred embodiment will now be described, by way of example, with reference to the accompanying drawings, in which:

FIG. 1B is a schematic representation of a typical heart signal as might be collected and analysed by the heart diagnosis system of the preferred embodiment of the present invention, the signal exhibiting the effects of heart murmurs;

DETAILED DESCRIPTION OF THE INVENTION

A heart diagnosis system according to a preferred embodiment of the present invention operates, broadly speaking, by:

a) acquiring heart sounds or signals from a patient's body;

b) amplifying and filtering the signals;

c) digitizing the amplified signals;

d) recording of the signals onto a computer;

e) pre-processing and filtering the recorded signals;

f) extracting desired features from the signals;

g) classifying the extracted signals for diagnosis;

h) interpreting the classified signals; and i) reporting the resulting diagnosis.

Figure 1A:
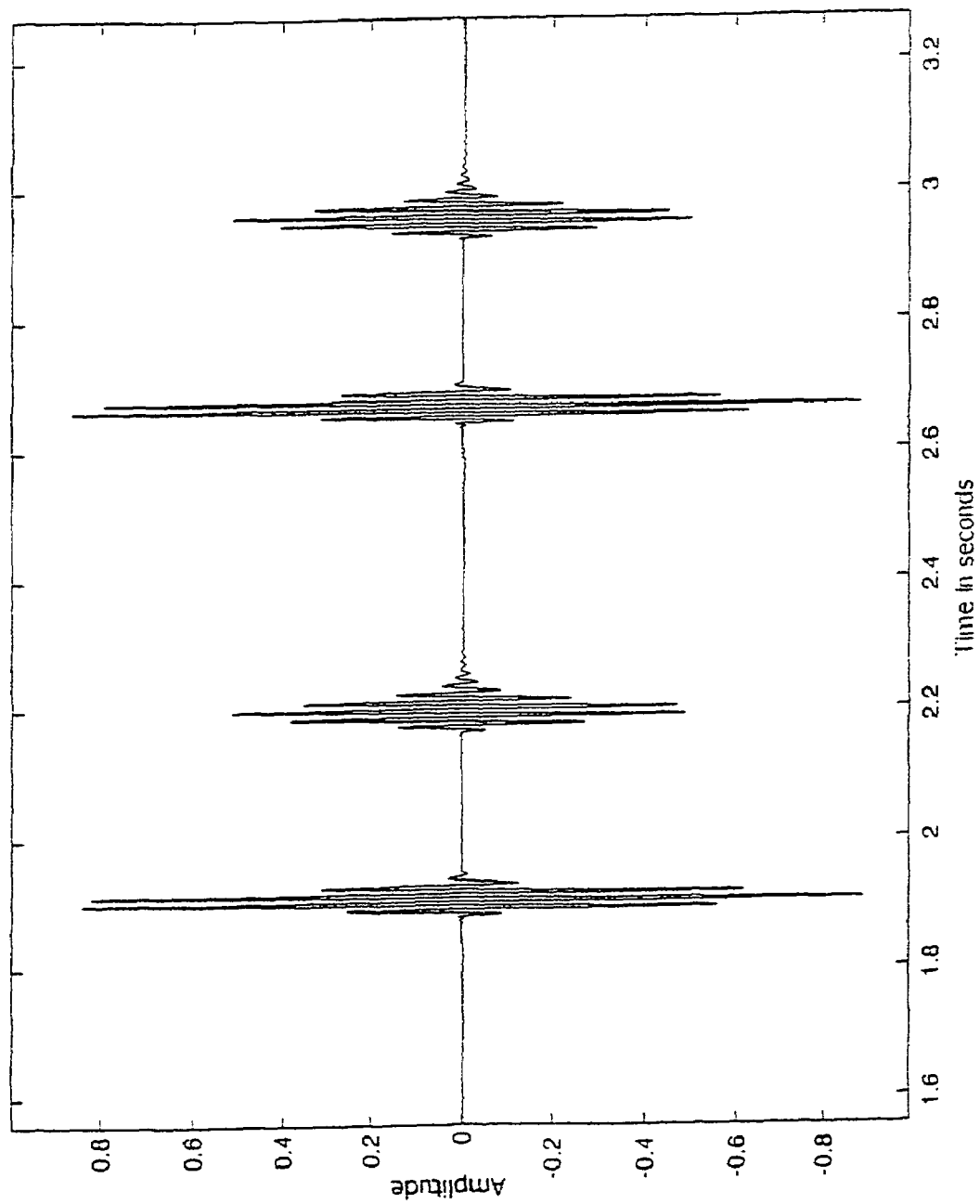
FIG. 1A is a schematic representation of a typical normal heart signal as might be collected and analysed by the heart diagnosis system of the preferred embodiment of the present invention.

FIG. 1A is a schematic representation of a typical normal heart signal; FIG. 1B is a similar representation of a heart signal from a heart with murmurs. These signals are typical of the sound signals collected by the present system. Heart sounds lie in the frequency range of 20 Hz to 2 kHz, with S1 in the range 30 to 110 Hz, S2 in the range 50 to 150 Hz, S3 approximately 30 Hz, S4 approximately 20 Hz, and heart murmurs anywhere in the range 20 Hz to 2 kHz.

Figure 2:
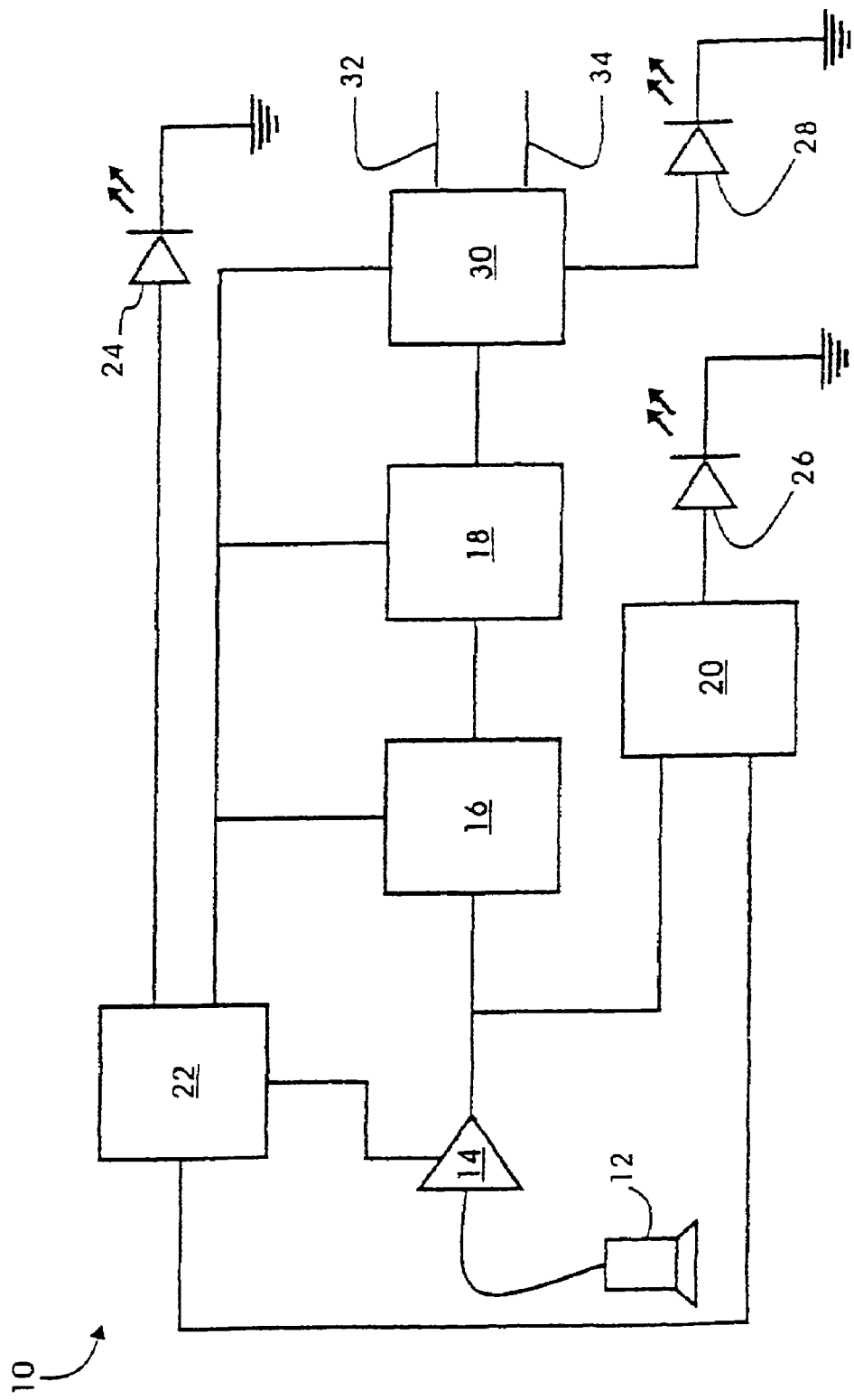
FIG. 2 is a schematic diagram of the data collection device of a heart diagnosis system according to a preferred embodiment of the present invention.

FIG. 2 is a schematic diagram of the data collection device 10 of the system of this embodiment. The data collection device 10 is connectable to a personal computer (also a part of the system); the data collection device includes a transducer in the form of sensor 12 for detecting the weak sounds between 20 Hz and 2 kHz made by the heart (sufficient for diagnosis of most diseases).

The sensor 12 receives the sound from the vibration of a diaphragm (not shown) provided adjacent to the sensor. The data collection device 10 converts the signals into electrical signals by means of the sensor 12, then amplifies the electrical signal by means of amplifier 14, removes unwanted noise, digitizes the signal by means of analog to digital converter (ADC) 16 and converts the signal to RS232 format for transmission to the computer. The device 10 uses the D9 serial port of the computer.

The device operates on a power supply in the form of single 9 V alkaline battery 22, and has a D9 male serial port to attach the serial port cord for the PC, one on/off switch to switch on/off the main power supply, and a three pin stereo connector to connect the sensor 12 to the amplifier 14. The AC mains are not used since they introduce a hum into the signal corresponding to the frequency of the mains (50 Hz in many countries), and medical equipment should be precise as possible and free from noise. The power supply 22 provides the voltages required by the device 10 (i.e. +5 V and −5 V to the amplifier 14, 1.5 V for the sensor 12 and 5 V for the digital section).

The device 10 also has a universal asynchronous receiver transmitter 18, a comparator 20 and three LEDs:

a) orange LED 24: glows whenever power is switched on;

b) red LED 26: glows flickeringly whenever the sensor is properly receiving sound signals from the heart, the flicker indicative of the heart signal; and c) green LED 28: glows when data is being transmitted to the computer.

Thus, as soon as the power is switched on orange LED 24 glows, indicating that the power is going to the hardware. Based on the intensity of the light glowing, the battery level will be known to the user. If the LED 24 glows low then it is time to change the battery 22. The signals are acquired from the hardware only when a signal comes from the computer. When this signal comes from the computer green LED 28 glows indicating that a signal is ready to be acquired. Once green LED 28 glows, the acquired signals are displayed in the monitor of the computer. The red LED 26 flickers according to the heart sounds. This LED 26 indicates whether the gain is sufficient or whether the gain has to be increased, and flickers owing to the signals coming out of a comparator 20. The amplified signals are sent to the comparator 20, whose first input is set at a standard voltage (viz. that of power supply 22) and whose second input receives the amplified signal. Whenever the signal level is above the preset value the red LED 26 flickers.

There is one switch for gain adjusting. This switch can be used if it is found that the signal being acquired by the computer is not of the expected level. This switch is used to reduce the gain if it is observed that the signal is clipped, and to increase the gain if the signal is very feeble (indicated by the red LED's not flickering).

Owing to the vibrations occurring on the diaphragm, sound is produced. This sound is picked up by the sensor. The sensor used is a condenser microphone which requires a supply of 1.5 V from the circuit itself. The sensor 12 is selected to give a good electrical signal based on the signal impinging on it.

The intensity of the sounds will vary from person to person. A thin person, for example, will have a high sound intensity, while for an overweight person the signals will have weak intensity. The signal must therefore be amplified to a optimum level by means of amplifier 14. The amplifier's basic functionality is to amplify the signal given to it in a ratio of the gain set by the user. This amplified signal has certain advantages, such as reduced noise and an increased signal strength lying in the input range of the ADC 16.

The ADC 16 converts the input analog signal into a digital signal using successive approximation registers commonly known as SARs. SAR ADCs are reliable and economical.

The ADC output is input into the UART 18. The UART's main function is to convert the signal from the ADC 16 into asynchronous or RS232 standard for subsequent transmission to the computer at a specified baud rate set for data processing.

If we speak or listen to music it is because the intensity of the sound is good enough to create disturbances in the medium and hence make an impression on our ears and a sound is heard.

As alluded to above, the device 10 also a serial port 30 for sending signals to (32) and receiving signals from (34) the PC.

Figure 3:
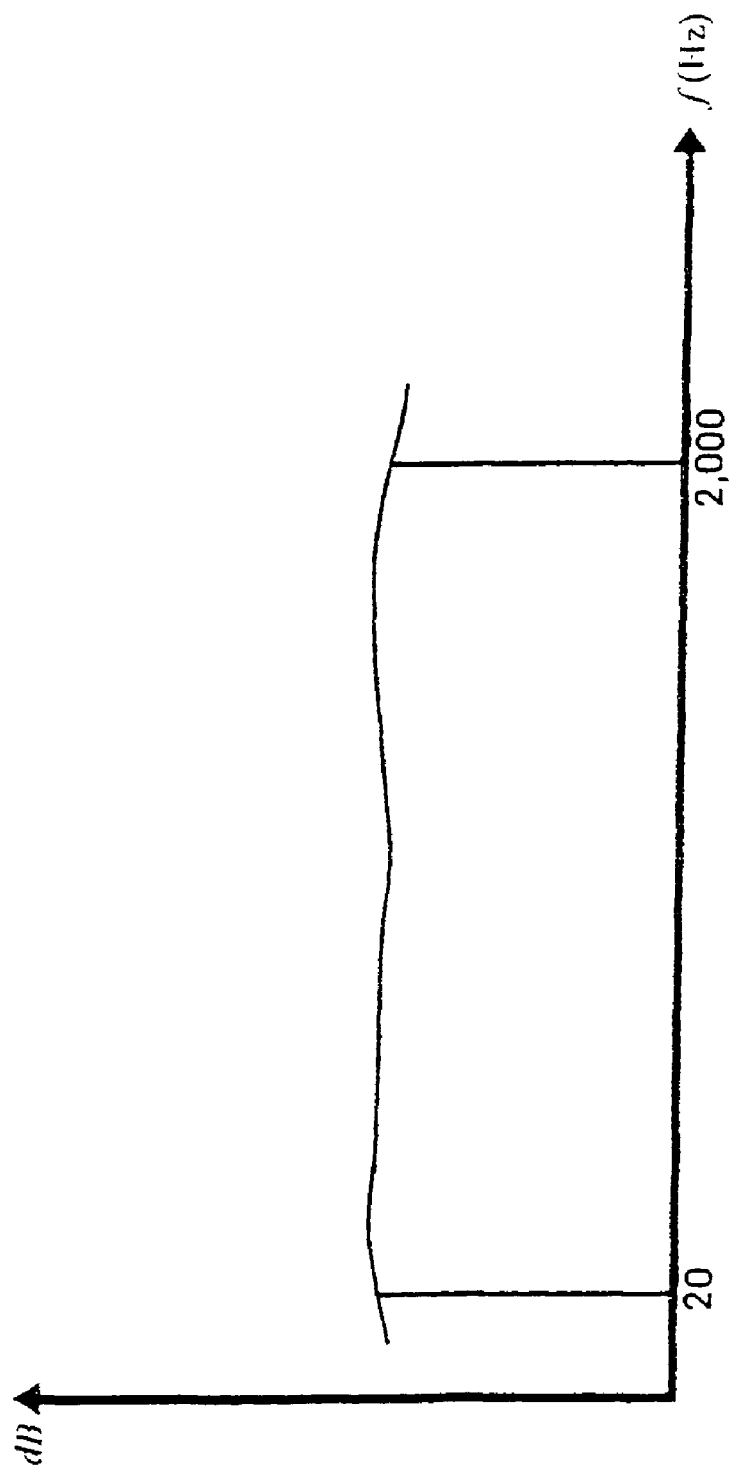
FIG. 3 is a schematic representation of the frequency response of the sensor of the data collection device of FIG. 2.

The intensity of heart sounds is very low, so various factors should be considered in the design of the sensor 12 of the present system. These factors include frequency response, voltage output of the sensor, unidirectionality, cost and availability. The sensor 12 should have consistent frequency response in the required frequency range, namely 20 Hz to 2 kHz. In other words the sensor should be able to pick up all the frequencies in the said range and should be able to give out similar response to all the frequencies. FIG. 3 is a schematic representation of the frequency response of the sensor 12 of the present system, plotted as amplitude against frequency.

The output of the sensor 12 is measured in volts/db/pascal, that is, the voltage per unit of intensity per unit pressure. Since the heart sounds are of very low intensity, the sensor 12 is able to detect the heart sounds and produce a strong output.

The sensor 12 is unidirectional in the sense that sound coming from one direction alone are converted to electrical signals and output. Its rejects—as far as possible—sounds coming from other directions.

Figure 4:
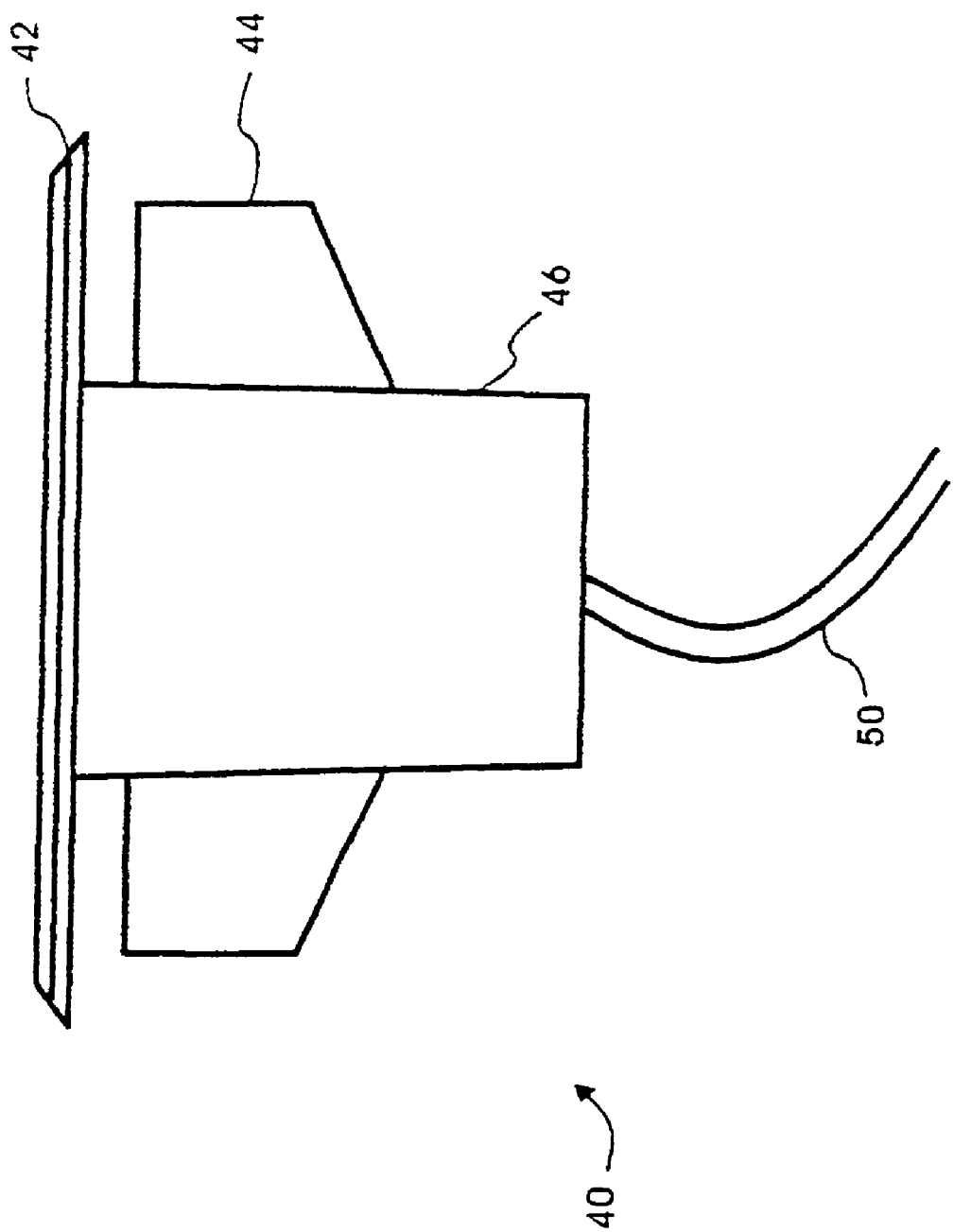
FIG. 4 is a schematically view of the chest piece of the system of the preferred embodiment.

The sensor 12 and its diaphragm are located in a chest piece, shown schematically at 40 in FIG. 4, which is similar in appearance to a stethoscope sensor, so patients are not disquieted by the use of unfamiliar equipment. The diaphragm 42 filters out high frequency noises, and the chest piece 40 is designed to prevent physical contact between the sensor 12 (within generally cylindrical portion 44) and the diaphragm 42. Further, the chest piece includes a sound damper between the sensor 12 and the chest piece walls, and is designed to be fixable to the patient (such as with a strap around a patient's upper body) by means of a buckle 46, so that—unlike a stethoscope—the examining person does not have to hold the chest piece in place.

Output cable 50 is also shown.

Figure 5A:
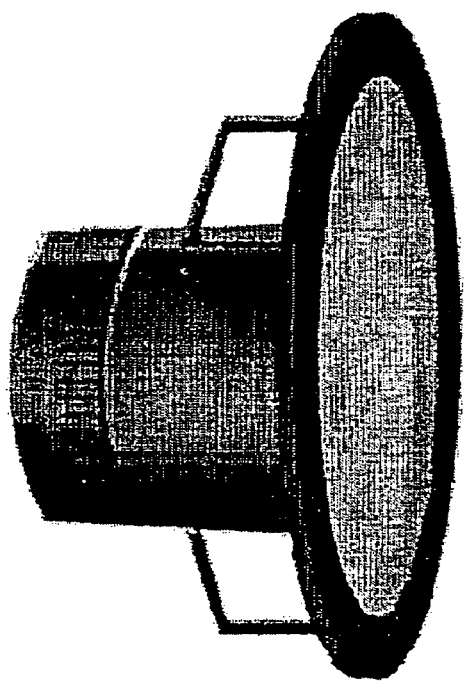
FIGS. 5A and 5B are twin perspective views of the chest piece of FIG. 4.
Figure 5B:
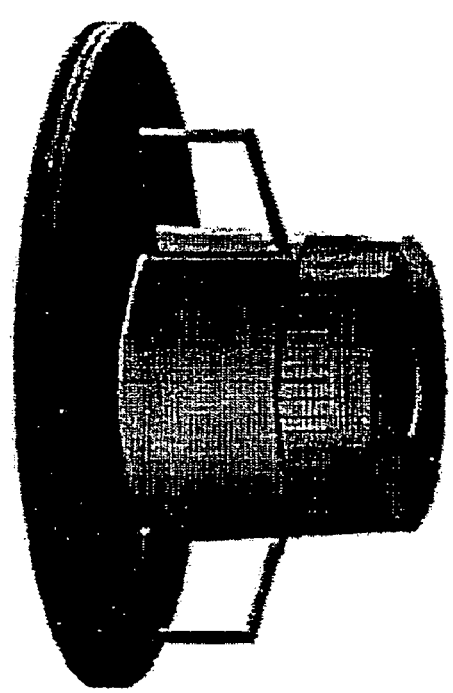

FIGS. 5A and 5B are twin perspective views of the chest piece 40, shown from two different angles. In FIG. 5A, the forward (patient contact) face of the diaphragm 42 is visible.

As mentioned above, the power supply 22 is in the form of a 9 V battery. As +5 V, −5 V, −9 V are required for the components used in the device 10, ICs with +9 V, −9 V, +5 V and −5 V outputs are employed.

Figure 6:
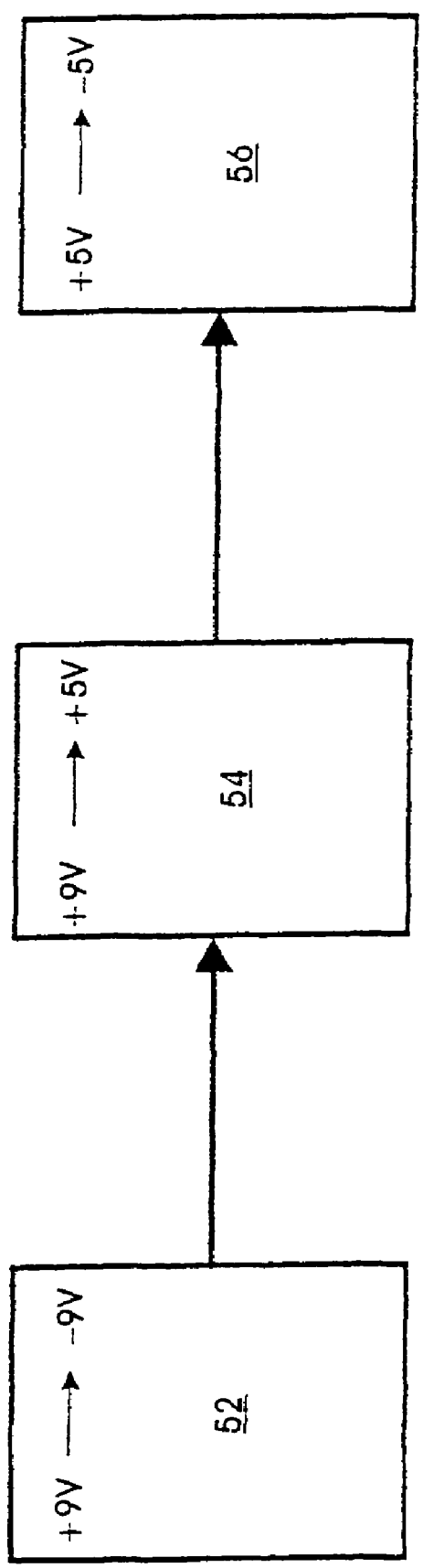
FIG. 6 is a schematic depiction of the process by which various voltages are provided by the one power supply in the sensor of the data collection device of FIG. 2.

The +9 V is made into +5 V using a voltage regulator and then given to the IC which has +5 V and −5 V outputs. The voltage converter IC is a charge pump converter: it uses a capacitor as a 'bucket' to pump charge from one place to another. Referring to FIG. 6, in this case the IC connects the positive terminal of first capacitor 52 to +9 V from the battery and its negative terminal to ground. First capacitor 52 charges up to 9 V from the battery 22. This IC then connects the positive terminal of first capacitor 52 to ground, and the negative terminal to pin 5. This lets first capacitor 52 dump the charge into second capacitor 54. The negative terminal of second capacitor 54 is tied to pin 5, so it gets a negative voltage equal to the voltage across first capacitor 52.

This charge pumping is a very efficient way to convert voltages. The only power lost is that power which is dissipated in the resistance of the switches inside the IC and the series resistance of the capacitors, as well as the power to run the internal oscillator that flips the switches when needed.

By itself, the IC runs at about 7 to 10 kHz, so there will be ripple of that amount on the output of second capacitor 54 and on the +9 V output from the battery 22 also. Audio equipment that uses this voltage could have an audible whine. However, the IC has a frequency boost feature. If pin 1 is connected to the power supply 22, the oscillator frequency goes up by about 6:1. The oscillator then works well above the audio region so that any whine will be inaudible.

Figure 7:
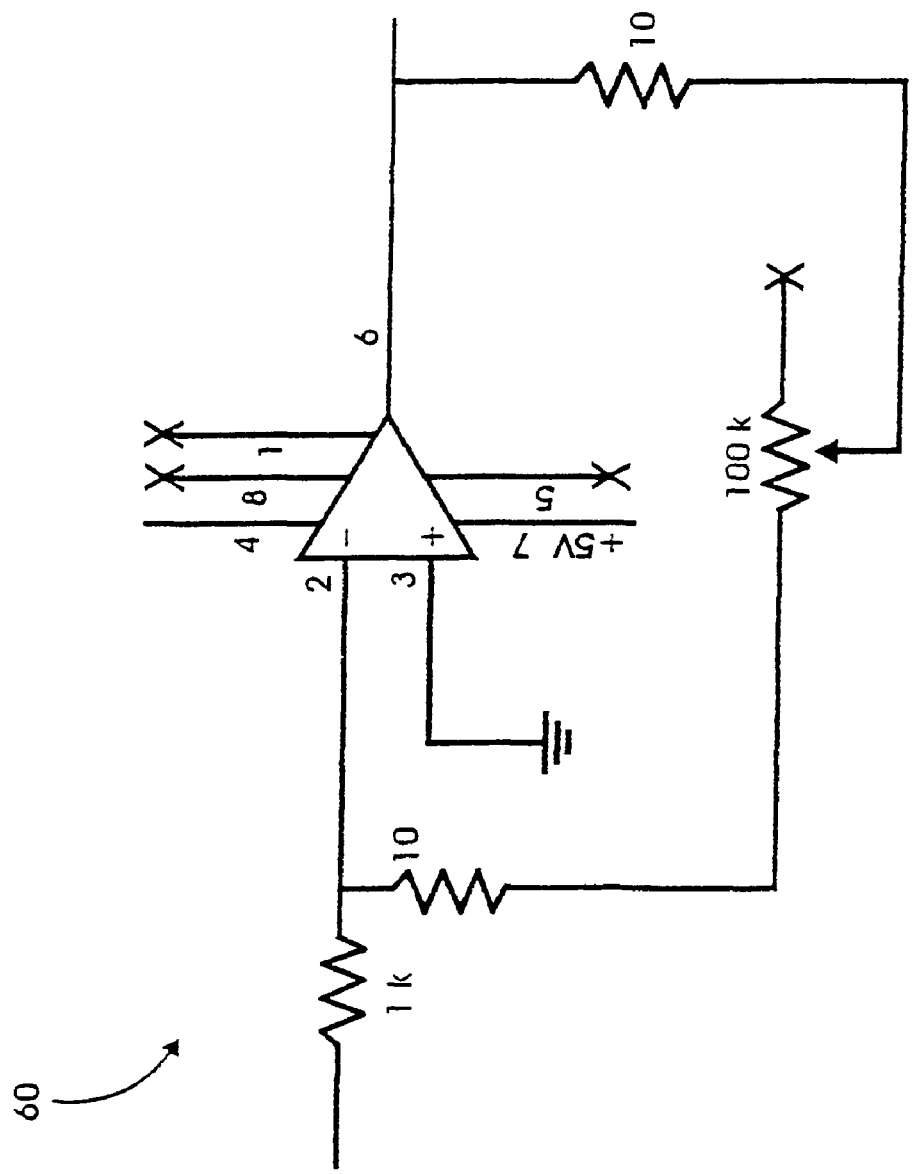
FIG. 7 is a schematic circuit diagram for the circuit of the amplifier of the data collection device of FIG. 2.

FIG. 7 is a schematic circuit diagram for the circuit 60 of amplifier 14. The circuit 60 provides a low noise transformerless amplifier, with a true-balanced circuit, sensor powering and high common mode rejection ratio. This design also includes sensor input loading of 1 kΩ. Input loading is capacitive reactive at higher frequencies to attenuate unwanted RF and ultrasonic signal at the input terminals. Sensor powering circuit provides power for sensor that require 1.5 V.

The signals coming from the sensor 12 are weak and have to be amplified. This is done using the amplifier circuit 60. The signals coming from the sensor are amplified based on the resistor combination. The amplifier design includes a gain switch in the form of potentiometer. As the potentiometer is adjusted the value of resistance changes and hence the gain increases or decreases based on the movement on the potentiometer. This gain can be adjusted based on the display in the monitor of the computer.

The amplifier used here has a good flat frequency response from 20 Hz to 2 kHz. The noise voltage at 1 kHz is 4 nV/sqrt (Hz) and the noise current at 1 khz is 0.4 pA/sqrt(Hz). The unity gain bandwidth of this amplifier is 10 MHz with a common mode rejection ratio of 100 db. It has a slew rate of 13 V/μs. It operates over a wide supply range of 3 V to 22 V.

Figure 8:
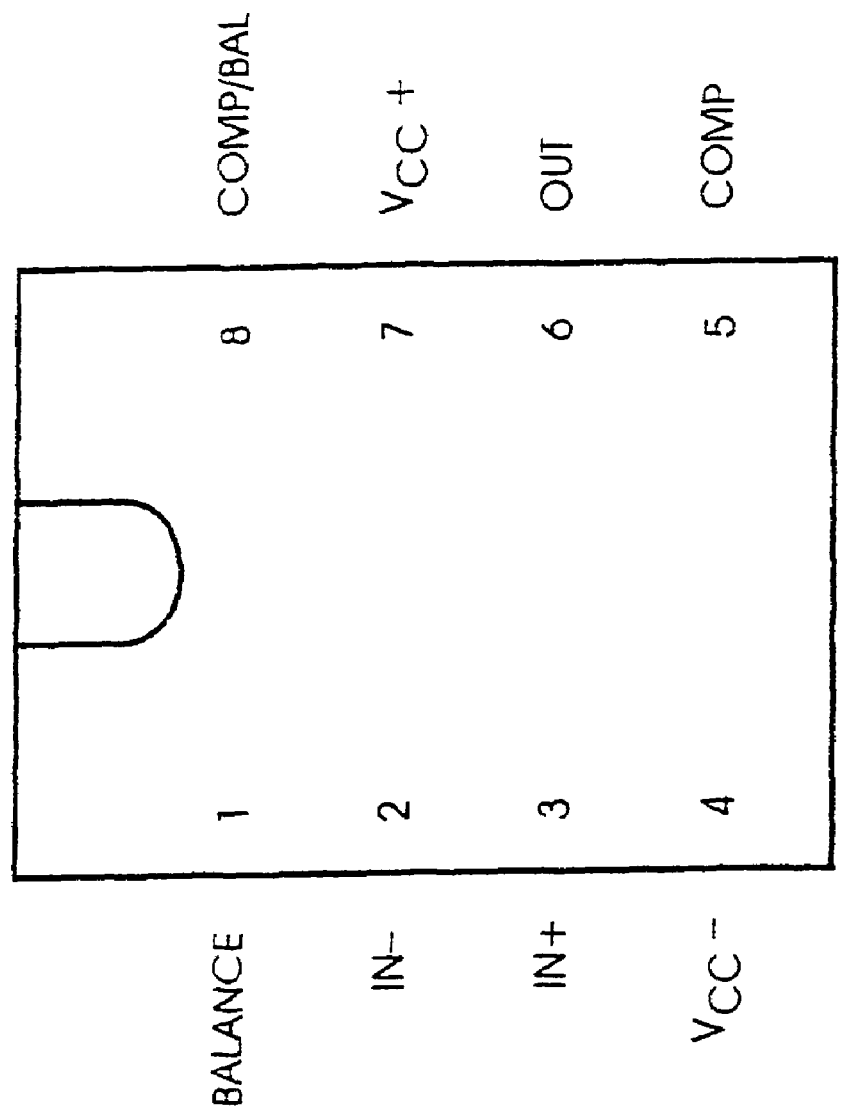
FIG. 8 is a view of the pin assignment of the IC of the amplifier of the data collection device of FIG. 2.

FIG. 8 is a view of the pin assignment of the amplifier IC.

Figure 9:
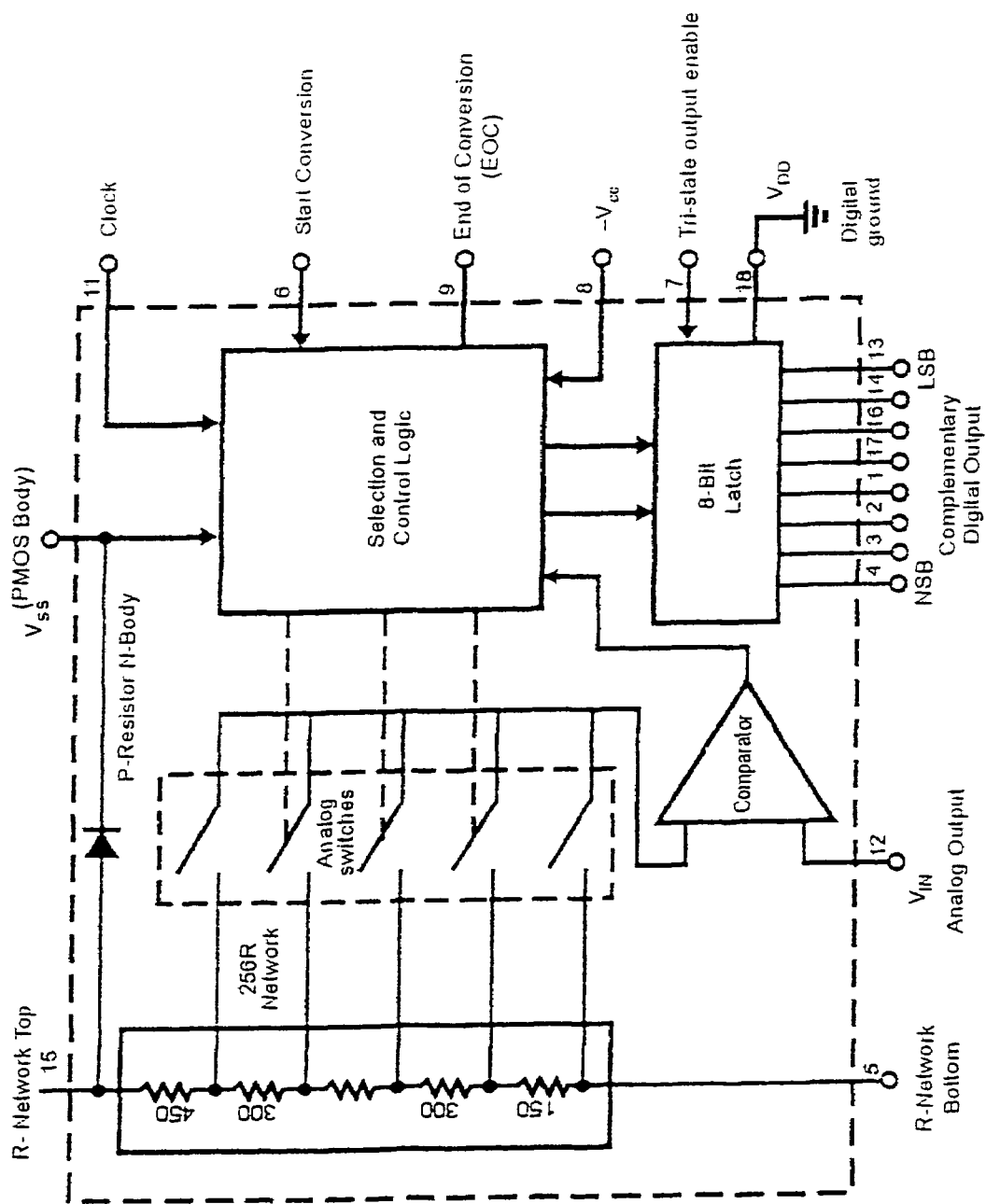
FIG. 9 is a pin diagram for the IC of the amplifier of the data collection device of FIG. 2.
Figure 10:
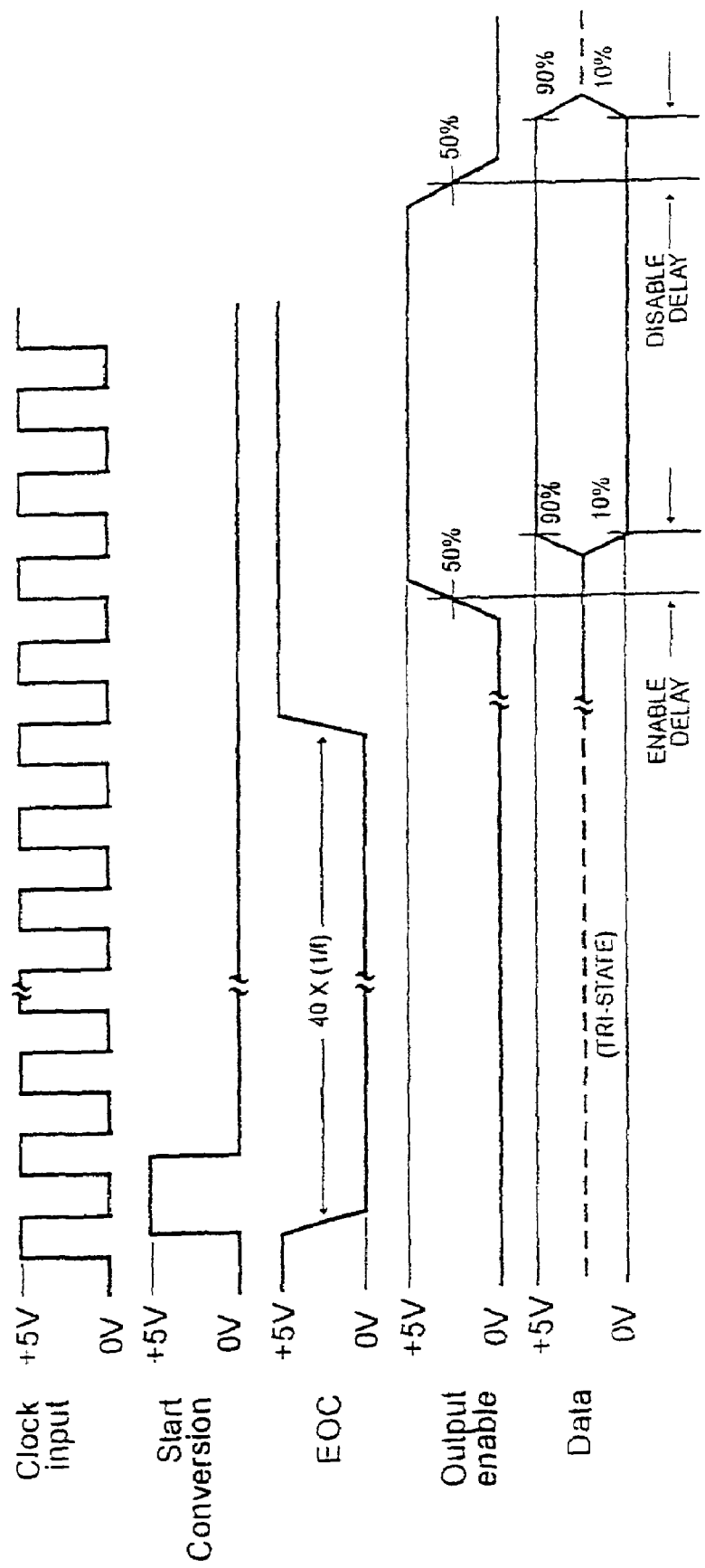
FIG. 10 is a timing diagram of the ADC of the data collection device of FIG. 2.

The ADC 16 has an input range of ±5 V, and a parallel interface. In order to meet this specification, the ADC is selected to have a conversion time of 47 clock cycles in free running mode. The pin diagram of the IC is as shown in FIG. 9, and the timing diagram of the ADC is shown in FIG. 10.

Figure 11:
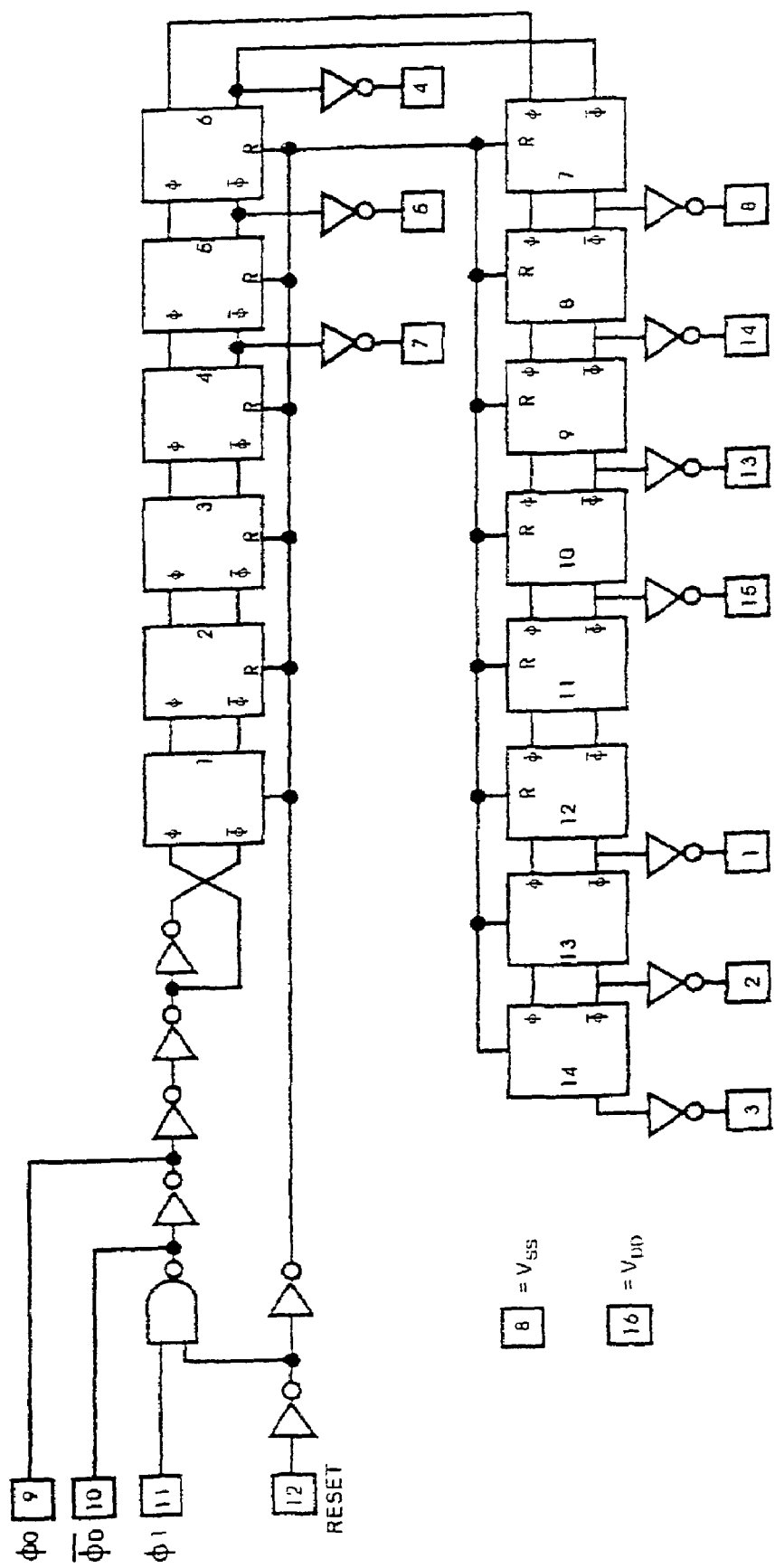
FIG. 11 is an internal diagram of the ADC of the data collection device of FIG. 2.

The ADC is placed in free running mode which gives the End of Conversion pulse after 47 clock cycles and starts the next conversion. The output of the ADC is an 8 bit which is a 256 combination output. The ADC clock is set to 270 kHz which is suitable to transfer the maximum of 2 kHz input signal. The clock calculation is derived from standard baud rate 57600. For 57600 baud rate, 5760 samples are transferred from UART 18 to the PC. In order to get the 5760 samples the ADC clock frequency is set to 270 kHz, that is, 5760×44. The ADC clock is derived from clock divider IC4060, which is a binary counter. The internal diagram of the ADC IC is shown in FIG. 11.

Figure 12:
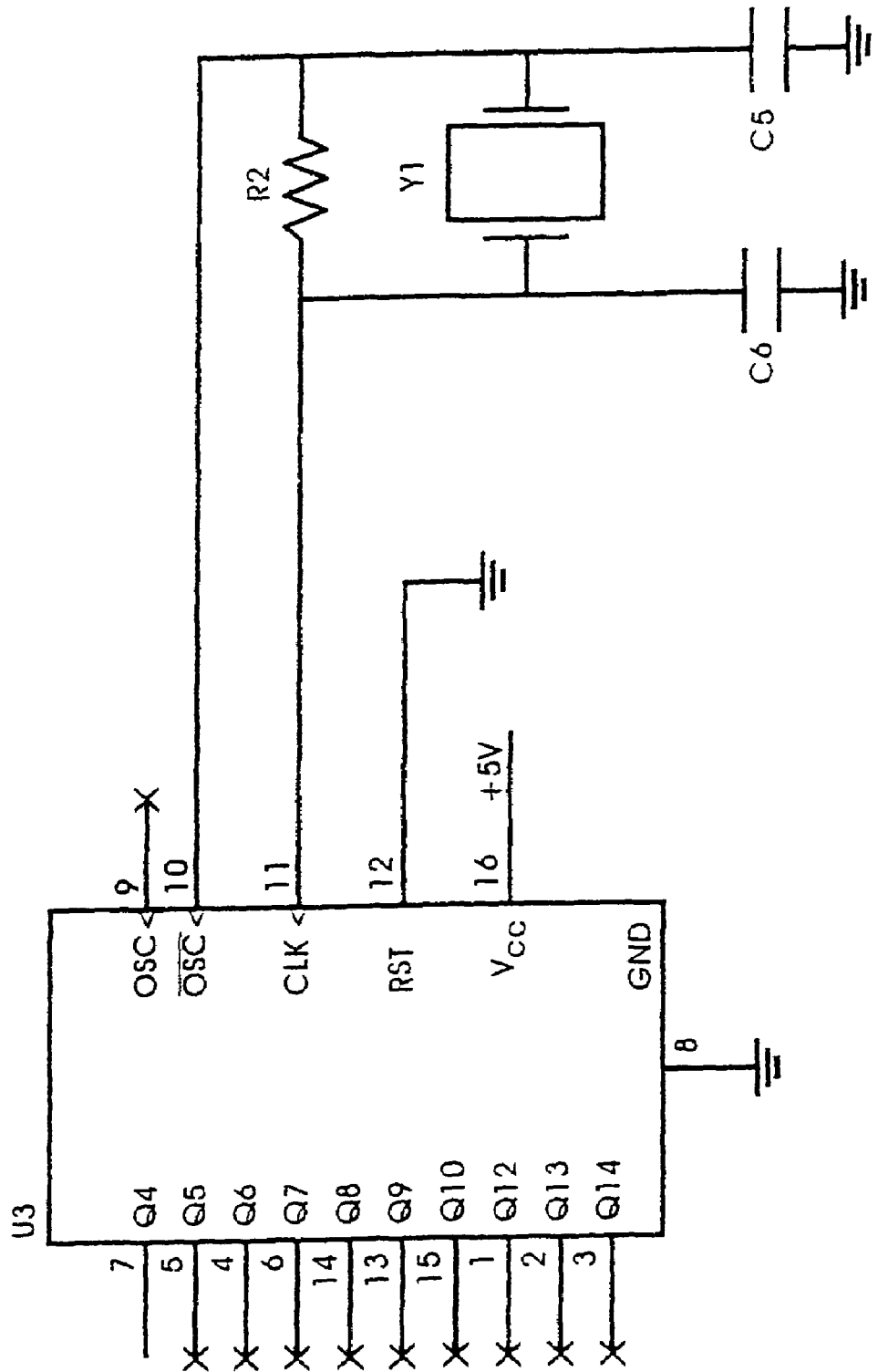
FIG. 12 is a connection diagram for the clock generator IC of the data collection device of FIG. 2.

To obtain the ADC clock 270 kHz, a crystal frequency of 270 kHz multiplied by 16 (giving 4.3 MHz) is used. The connection diagram of the clock generator IC is as shown in FIG. 12.

The specification for serial ports, as used in this system, is provided in the EIA (Electronics Industry Association) RS232C standard. It states many parameters, including:

1. A 'Space' (logic 0) will be between +3 and +25 V;

2. A 'Mark' (Logic 1) will be between −3 and −25 V;

3. The region between +3 and −3 volts is undefined;

4. An open circuit voltage should never exceed 25 V (in Reference to GND); and

5. A short circuit current should not exceed 500 mA.

The driver should be able to handle this without damage.

Serial ports come in two sizes: D-Type 25 pin connectors and D-Type 9 pin connectors. Both are male on the back of the PC, so a female connector is used on the peripheral device. Table 1 lists pin connections for the 9 pin and 25 pin D-Type connectors.

TABLE 1

D Type 9 Pin and D Type 25 Pin Connectors

| D-Type-25 Pin No. | D-Type-9 Pin No. | Abbreviation | Full Name |
|---|---|---|---|
| Pin 2 | Pin 3 | TD | Transmit Data |
| Pin 3 | Pin 2 | RD | Receive Data |
| Pin 4 | Pin 7 | RTS | Request To Send |
| Pin 5 | Pin 8 | CTS | Clear To Send |
| Pin 6 | Pin 6 | DSR | Data Set Ready |
| Pin 7 | Pin 5 | SG | Signal Ground |
| Pin 8 | Pin 1 | CD | Carrier Detect |
| Pin 20 | Pin 4 | DTR | Data Terminal Ready |
| Pin 22 | Pin 9 | RI | Ring Indicator |

Figure 13:
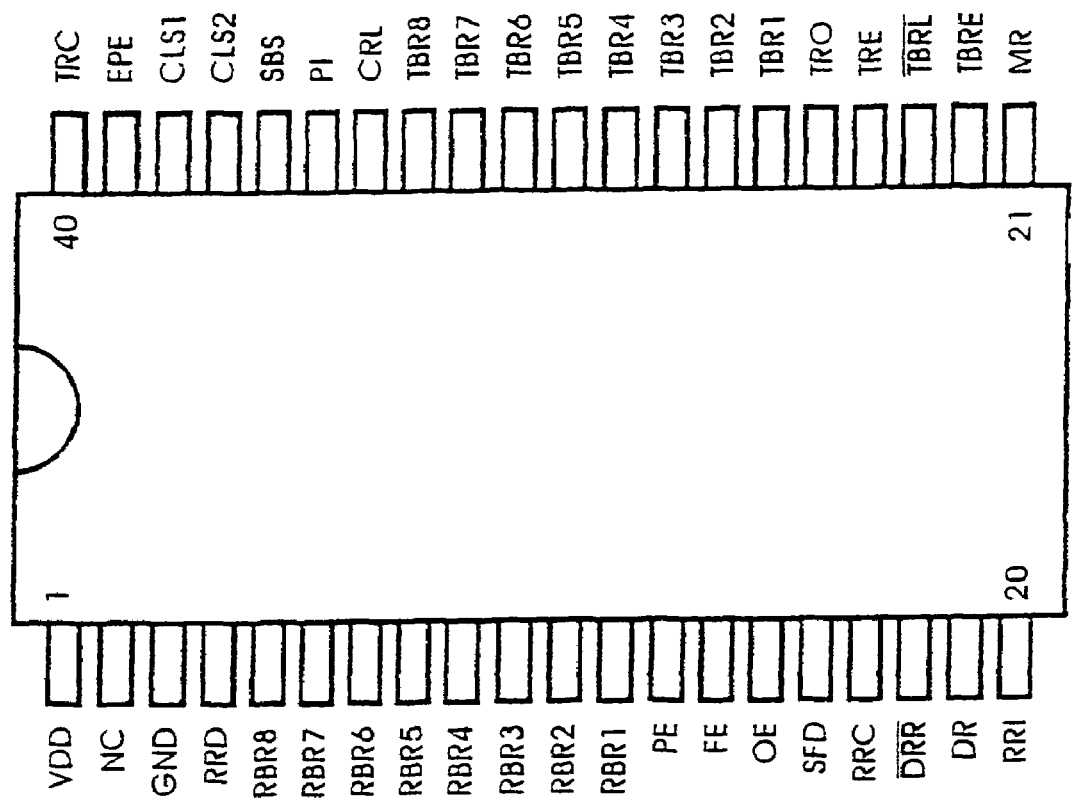
FIG. 13 depicts the pin assignments of the UART of the data collection device of FIG. 2.

The UART's Control Register is made up of Parity Inhibit (PI), Stop Bit Select (SBS), Character Length Select (CLS1 and 2) and Even Parity Enable (EPE). These inputs can be latched using the Control Register Load (CRL) or if this pin is tied to high, changes made to these pins will immediately take effect. The pin assignments of the UART 18 are shown in FIG. 13, and listed in Table 2.

TABLE 2

Pin Description for UART

| PIN | ABBR. | FULL NAME | NOTES |
|---|---|---|---|
| 1 | VDD | +5 V Supply Rail | |
| 2 | NC | Not Connected | |
| 3 | GND | Ground | |
| 4 | RRD | Receiver Register Disable | When driven high, outputs RBR8: RBR1 are High Impedance. |
| 5:12 | RBR8, RBR1 | Receiver Buffer Register | Receiver's data bus |
| 13 | PE | Parity Error | When High, a parity error has occurred. |
| 14 | FE | Framing Error | When High, a framing error has occurred, i.e. the stop bit was not a logic 1. |
| 15 | OE | Overrun Error | When High, Data has been received but the nData Received Reset had not yet been activated. |
| 16 | SFD | Status Flag Disable | When High, Status Flag Outputs (PE, FE, OE, DR and TBRE) are High Impedance. |
| 17 | RRC | Receiver Register Clock | ×16 Clock input for the Receiver Register. |
| 18 | nard | Data Received | Active Low. When low, sets Data received Output Low (i.e. Clears DR) |
| 19 | DR | Data Received Reset | When High, data has been received and placed on outputs RBR8:RBR1. |
| 20 | RRI | Receiver Register | RXD—Serial Input. Connect to Serial Port, Via RS 232 receiver. |
| 21 | MR | Master Reset | Resets the UART. UART |

TABLE 2-continued

Pin Description for UART

| PIN | ABBR. | FULL NAME | NOTES |
|---|---|---|---|
| | | Register | should be reset after applying power. |
| 22 | TBRE | Transmitter Buffer Register | Empty when High, indicates that transmitter buffer register is empty, thus all bits including the stop bit have been sent. |
| 23 | nTBRL | Transmitter Buffer Load/Strobe | Active Low. When low, data present on TBR8: TBR1 is placed in Transmitter Buffer Register. A Low to High Transition on this pin, then sends the data. |
| 24 | TRE | Transmitter Register Empty | When High, Transmitter Register is Empty, thus can accept another byte of data to be sent. |
| 25 | TRO | Transmitter Register Out(TXD) | TXD—Serial Output. Connect to Serial Port, via RS-232 Transmitter. |
| 26:33 | TBR8: TBR1 | Transmitter Buffer Register | Data Bus, for Transmitter. Places Data here. |
| 34 | CRL | Control Register Load | When High, Control Register (PI, SBS, CLS2, CLS1, EPE) is Loaded. Can be tied high, so changes on these pins occur instantaneously. |
| 35 | PI | Parity Inhibit | When High, No Parity is Used for Both Transmit and Receive. When Low, Parity is Used. |
| 36 | SBS | Stop Bit Select | A High selects 2 stop bits. (1.5 for 5 Character Word Lengths) A Low selects one stop bit. |
| 37:38 | CLS2: CLS1 | Character Length Select | Selects Word Length. 00 = 5 Bits, 01 = 6 Bits, 10 = 7 Bits and 11 = 8 Bits. |
| 39 | EPE | Even Parity Enable | When High, Even Parity is Used, When Low, Odd Parity is Used. |
| 40 | TRC | Transmitter Register Clock | 16× Clock input for Transmitter. |

The clock divider IC has Q4 to Q14 available for use as they have external connections. This means higher Baud Rates are not obtainable from common crystals, such as the 14.31818 MHz. The UART requires a clock rate 16 times higher than the Baud Rate you will be using. A baud rate of 57600 bps, for example, requires an input clock frequency of 921.6 kHz.

The CMOS UART can handle up to 200 kbps at 5 V, but the level converter may be limited to 120 kbps, which is still within range. In PC maximum available standard baud rate is 115200; the next available baud rate is selected to be 56700.

Signal Processing

Figure 14:
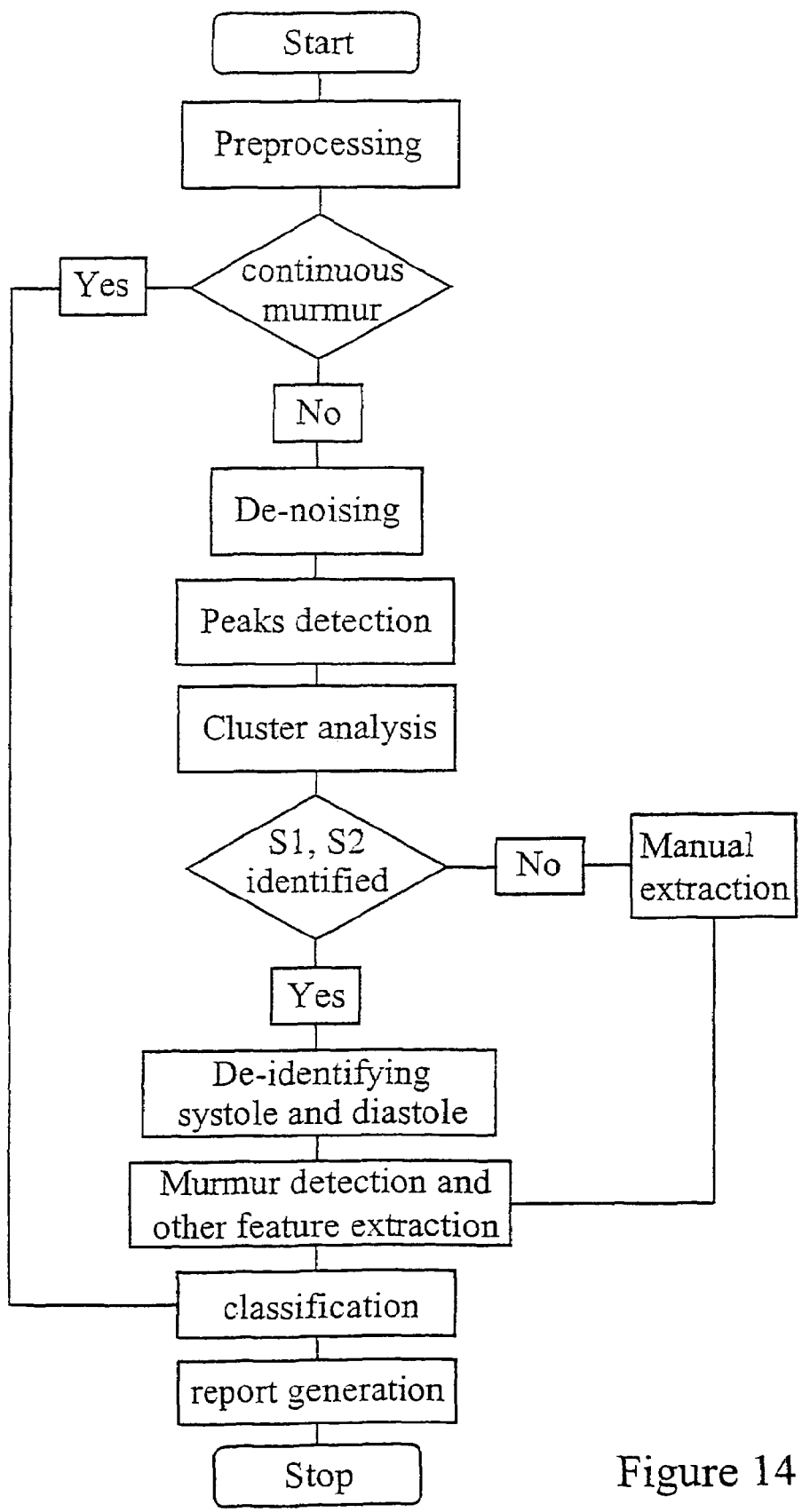
FIG. 14 is a flow diagram of the full signal processing performed by the system of the present embodiment.

The collected signal includes noise, motion artifacts, breathing sounds and other background sounds. In order to correctly identify the actual heart sounds, the systole and diastole regions are first identified. By finding the first and seconds heart sounds the systole and diastole regions can be found. FIG. 14 is a flow diagram of the full signal processing performed by the system of the present embodiment, as is described in detail below.

The heart sounds contain frequency components from 20 Hz to 2 kHz with much of its frequency components below 1 kHz. The signals are sampled at 7200 Hz. Since the signal is sampled at a high frequency, the signal contains much redundant information. According to the Nyquist criterion, it is sufficient to sample a signal at twice the maximum frequency component present. In the present case, therefore, it is sufficient to sample the signal at 4 kHz. If the raw signal is not down sampled, the processing time will be significantly higher, so the signal is down sampled to 4 kHz.

The system supports the file formats WAV (Windows PCM Wav Format), AU and MAT (Matlab MAT file).

Since the intensity of the heart beat is variable, the signal amplitude is normalized to between +1 and −1. Thus, during preprocessing the raw signal is converted to a 4 kHz normalized signal. The signal is then available in the form of a matrix suitable for further processing.

The first and second heart sounds have their energies concentrated in the 30 to 150 Hz region. Unfortunately motion artifacts and background noise fall in essentially the same frequency range. Consequently, it is difficult to remove the noise by conventional noise removal techniques so wavelet based techniques are employed in the present system.

The general de-noising procedure involves three steps. Firstly, a wavelet is chosen and the signal is decomposed to N levels. Secondly, for each level from 1 to N, a threshold is selected and applied to the detail coefficients. Thirdly, the wavelet reconstruction is computed using the original approximation coefficients of level N and the modified detail coefficients of levels from 1 to N.

The 'hard' threshold signal is x if $|x|>t$, and is 0 if $|x|<=t$. The 'soft' threshold signal is $sign(x) (|x|-t)$ if $|x|>t$ and is 0 if $|x|<=t$.

Hard thresholding is the usual process of setting to zero the elements whose absolute values are lower than the threshold. Soft thresholding is an extension of hard thresholding, in which the elements whose absolute values are lower than the threshold are first set to zero, and then the nonzero coefficients are shrunk towards 0.

Figure 15C:
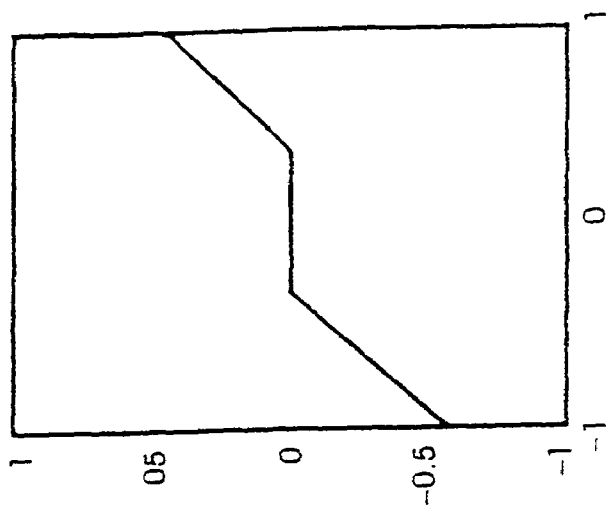
FIG. 15C is a plot of a soft thresholding signal corresponding to the signal of FIG. 15A.
Figure 15B:
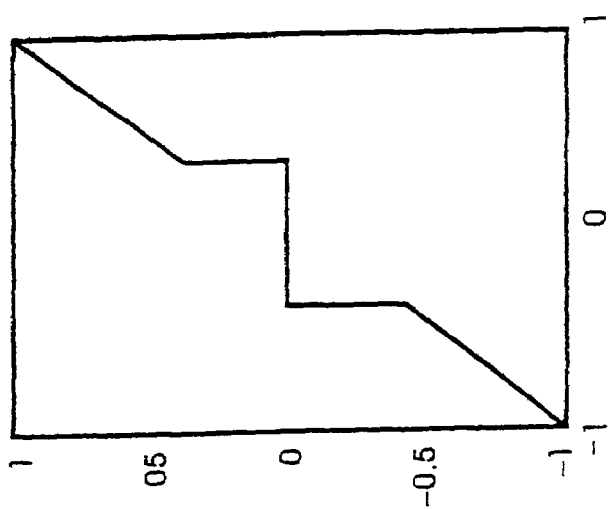
FIG. 15B is a plot of a hard thresholding signal corresponding to the signal of FIG. 15A.
Figure 15A:
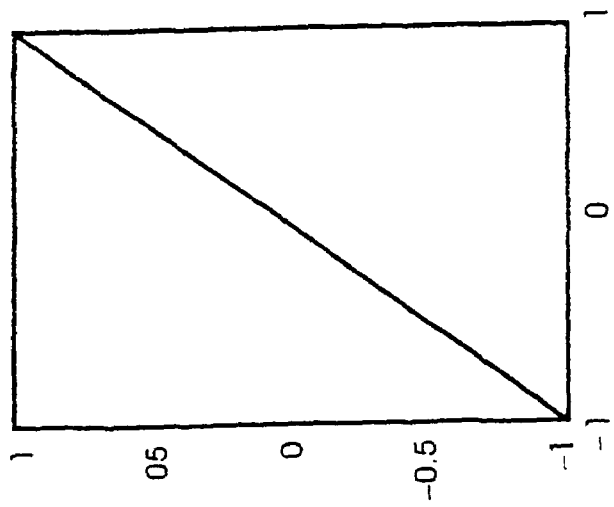
FIG. 15A is a plot of a notional original signal to be processed by the system of the preferred embodiment.

FIG. 15A illustrates a notional original signal; the corresponding hard thresholding signal is shown in FIG. 15B, and the corresponding soft thresholding signal is shown in FIG. 15C.

Figure 16A:
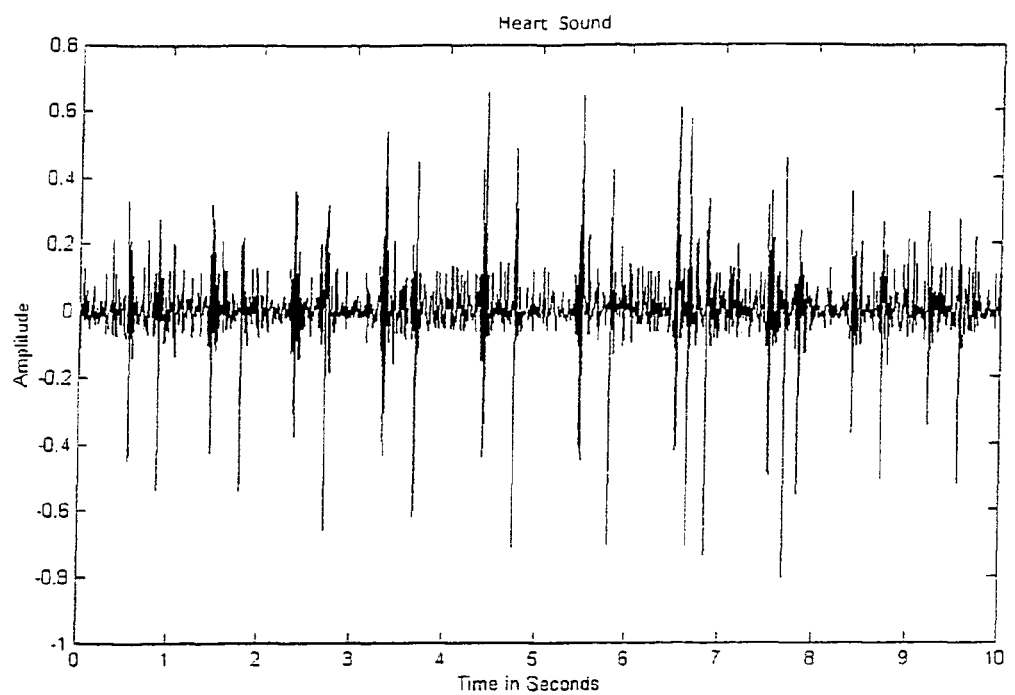
FIG. 16A is a heart signal before de-noising.
Figure 16B:
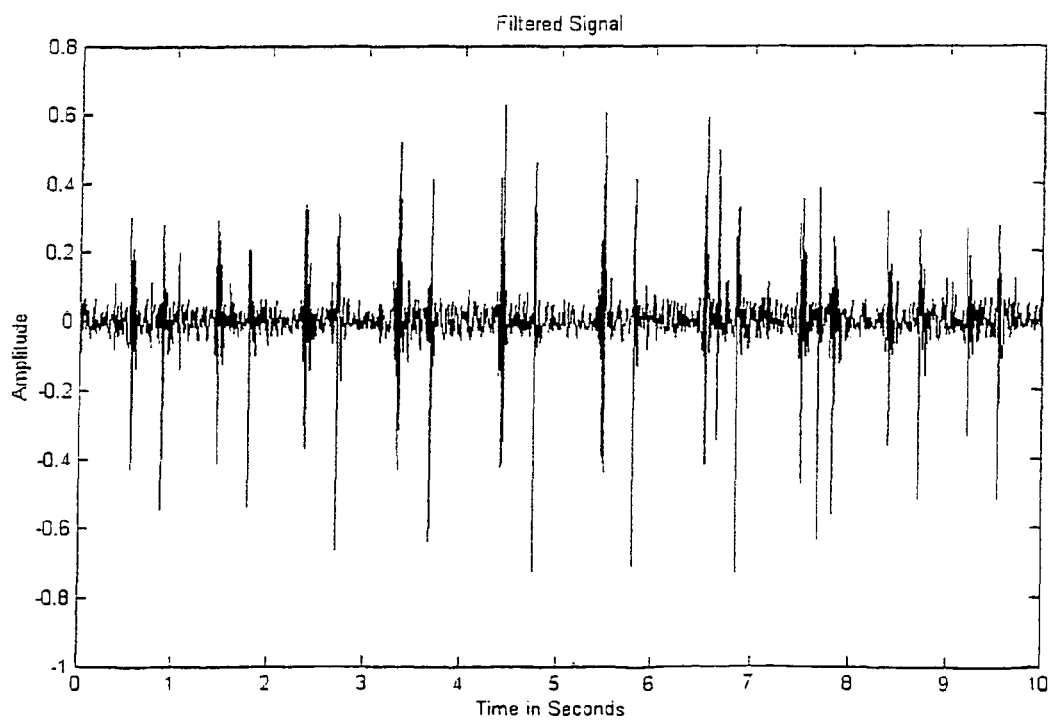
FIG. 16B is the heart signal of FIG. 16A after de-noising by the system of the preferred embodiment.

In choosing the threshold rules one can afford to lose the information contained in the murmur frequencies, as the principal aim is to enhance the first and second heart sounds (S1 and S2) to enable their successful extraction. Consequently, the decomposition levels that do not contribute to the first and second heart sounds are neglected when framing the threshold rules, and the output of the de-noise module is the raw input waveform whose first and second heart sounds are enhanced with all other unwanted components removed. FIGS. 16A and 16B are, respectively, a heart signal before and after de-noising plotted in each case as amplitude versus time.

After de-noising the prominent heart sounds are identified, which involves identifying the peaks in the signal. The peaks are regions where the amplitude of the signal is high. It is generally not possible to identify the peaks directly from the signal as they contain high amplitude oscillations. However, the peaks can be identified by filtering the signal and then calculating its envelope. The latter is done by calculating the signal's Shannon's energy is calculated, which clearly amplifies the peaks while suppressing other regions.

Figure 17:
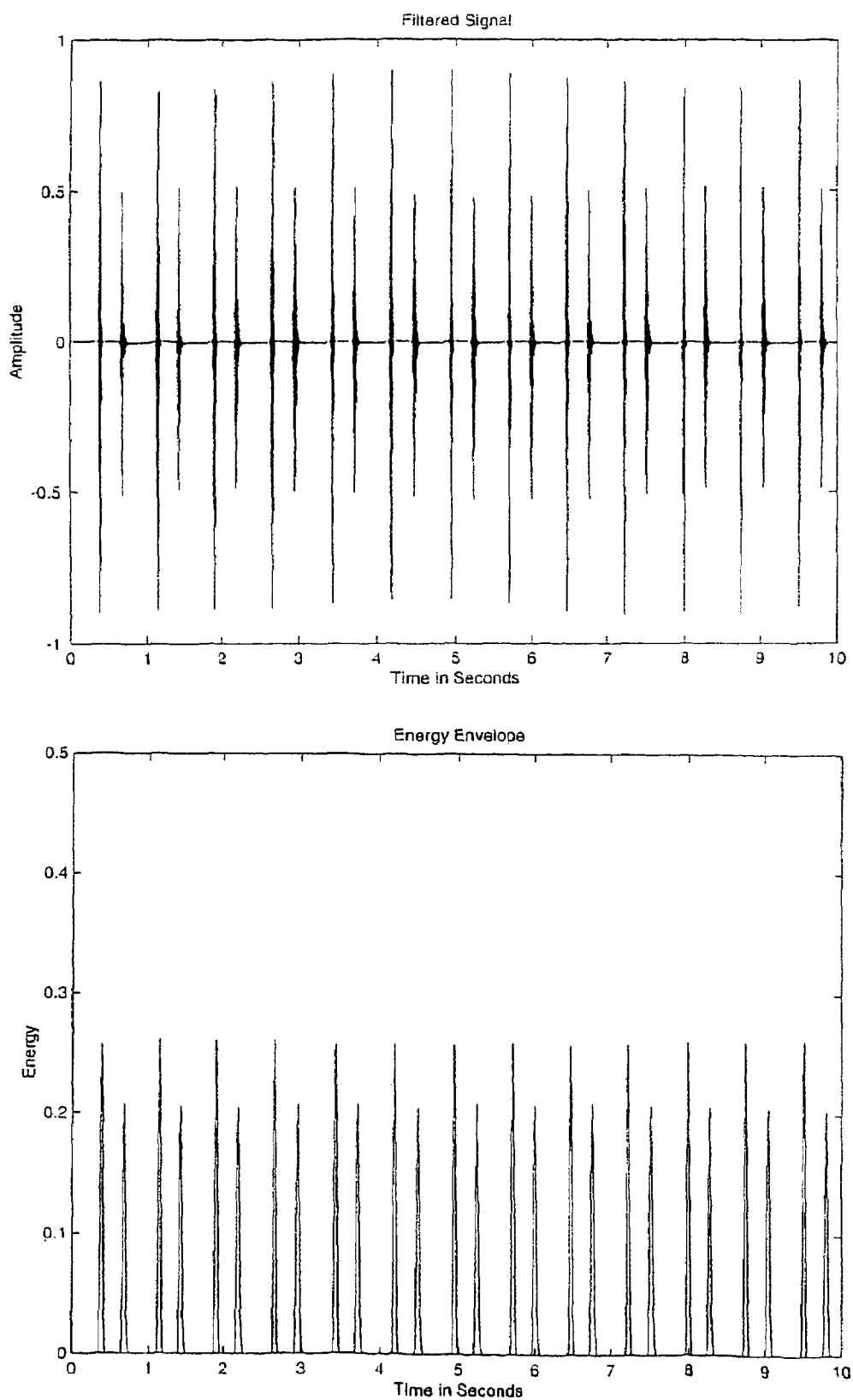
FIG. 17 is a plot a filtered signal (top) and a signal energy envelope (bottom) determined according to the system of the preferred embodiment.

FIG. 17 includes plots of a filtered signal (top: amplitude versus time) and signal energy envelope (bottom: energy versus time).

The maximum amplitude of the signal is calculated for every one second of the envelope signal. The values of the envelope signal above certain percentage of the maximum value are separated. These values represent the peaks with zero values between them. Then the starting and ending point of these peaks are identified.

After prominent peaks have been identified, the following peak parameters are calculated:

1. Maximum value;

2. Area of the peak;

3. Width of the peak;

4. Starting point of the peak;

5. Ending point of the peak; and

6. Distance to the successive peak.

The cluster analysis of the peaks is performed based on the following peak parameters:

1. Maximum Amplitude of the peak;

2. Width of the peak;

3. Area of the peak; and

4. Distance to the successive peak.

Cluster analysis has been found to eliminate false peaks due to motion artifacts and breathing sounds that have escaped the de-noising process; the former are random and give rise to dissimilar peaks, and are readily eliminated by cluster analysis. Breathing sounds may produce false peaks with a higher degree of similarity, but it has been found that the maximum amplitude or width of such peaks have a low degree of similarity when compared to peaks of the first and second heart sounds, so are also eliminated by cluster analysis.

The method proceeds by:

1. Finding the similarity or dissimilarity between every pair of objects in the data set;

2. Grouping the objects into a binary, hierarchical cluster tree; and

3. Determining where to divide the hierarchical tree into clusters.

To find the similarity or dissimilarity, the distance between objects is calculated, in one of a variety of ways. In the present system, the aim is to calculate the Euclidean distance between objects in a data set of m objects, or pairs $m(m-1)/2$ pairs of objects. The result of this computation is commonly known as a similarity matrix (or dissimilarity matrix). In a real world data set, variables can be measured against different scales; here each of the parameters has a different amplitude. All the values in the data set are converted to the same proportional scale. At the end of this step the distance between every pair of objects is found.

In this case the 'distance to the successive peak' is the important parameter. This parameter shows a very high degree of similarity for the peaks due to the first and second heart sounds, owing to the fact that systole and diastole periods are relatively constant and systole period is always lesser than the diastole period. This being the case, it is reasonable to assume that the distance between successive S1 peaks and S2 peaks forms two clusters with a high degree of similarity. If there is a recurring third heart sound it will form another cluster.

Figure 18:
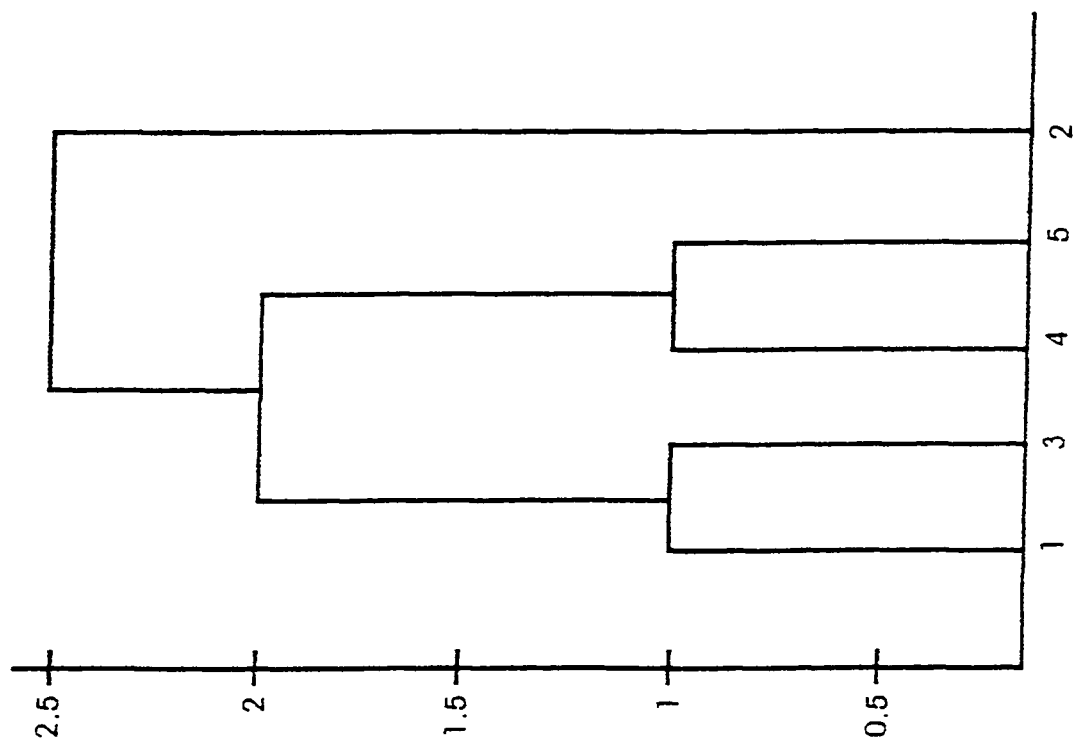
FIG. 18 is a dendrogram obtained in the cluster analysis of a heart signal according to the system of the preferred embodiment.

To group the objects, pairs of objects that are in close proximity are linked together using the linkage function. Once the proximity between objects in the data set has been computed, it is possible to determine which objects in the data set should be grouped together into clusters, using the linkage function. The linkage function takes the distance information and links pairs of objects that are close together into binary clusters (clusters made up of two objects). The linkage function then links these newly formed clusters to other objects to create bigger clusters until all the objects in the original data set are linked together in a hierarchical tree. The hierarchical, binary cluster tree created by the linkage function is most easily understood when viewed graphically as a dendrogram, as shown in FIG. 18; the horizontal axis represent the indices of the objects in the original data set. The links between objects are represented as upside down U-shaped lines. The height of the U indicates the distance between the objects. For example, the link representing the cluster containing objects 1 and 3 has a height of 1.

In determining where to divide, the linkage function uses the distance information generated in step 1 to determine the proximity of objects to each other. As objects are paired into binary clusters, the newly formed clusters are grouped into larger clusters until a hierarchical tree is formed in the hierarchical cluster tree, the data set may naturally align itself into clusters. This can be particularly evident in a dendrogram diagram where groups of objects are densely packed in certain areas and not in others.

The inconsistency coefficient of the links in the cluster tree can identify these points where the similarities between objects change. In our program the after finding the distance information, the inconsistency coefficient is calculated. Then the objects are grouped in to clusters.

In the typical data set there may be one, two or more groups. If the signal has S1 and S2 alone, the two natural clusters may be formed. If the signal includes other heart sounds then there may be more than 2 clusters. The inconsistent function gives the inconsistency values for each links. By setting the maximum value of the inconsistent matrix as threshold the natural divisions in the data set can be identified. If the peaks cannot be grouped, the system software indicates that automatic extraction is not possible and that manual extraction is performed.

After identifying the different groups in the peaks, the peaks are identified as S1, S2 or other heart sounds based on the previously estimated parameters; for example, S1 generally has a shorter 'distance to successive peak' than S2. If the signal has first, second and any third heart sounds, each of the three sounds will be grouped as three separate clusters. The heart sounds may be S3, S4, ejection click, opening snap, pericardial rub, tumor plops. Each of these sounds will differ in at least any one of the above mentioned parameters. By considering these four parameters each group can be identified. In this way all the groups are identified. Of course, the systole and diastole regions include the first and second heart sounds, but for the present purposes the systole region is taken to be the region between the end of S1 and the beginning of S2, the diastole region the region between the end of S2 and the beginning of the next S1.

Figure 19:
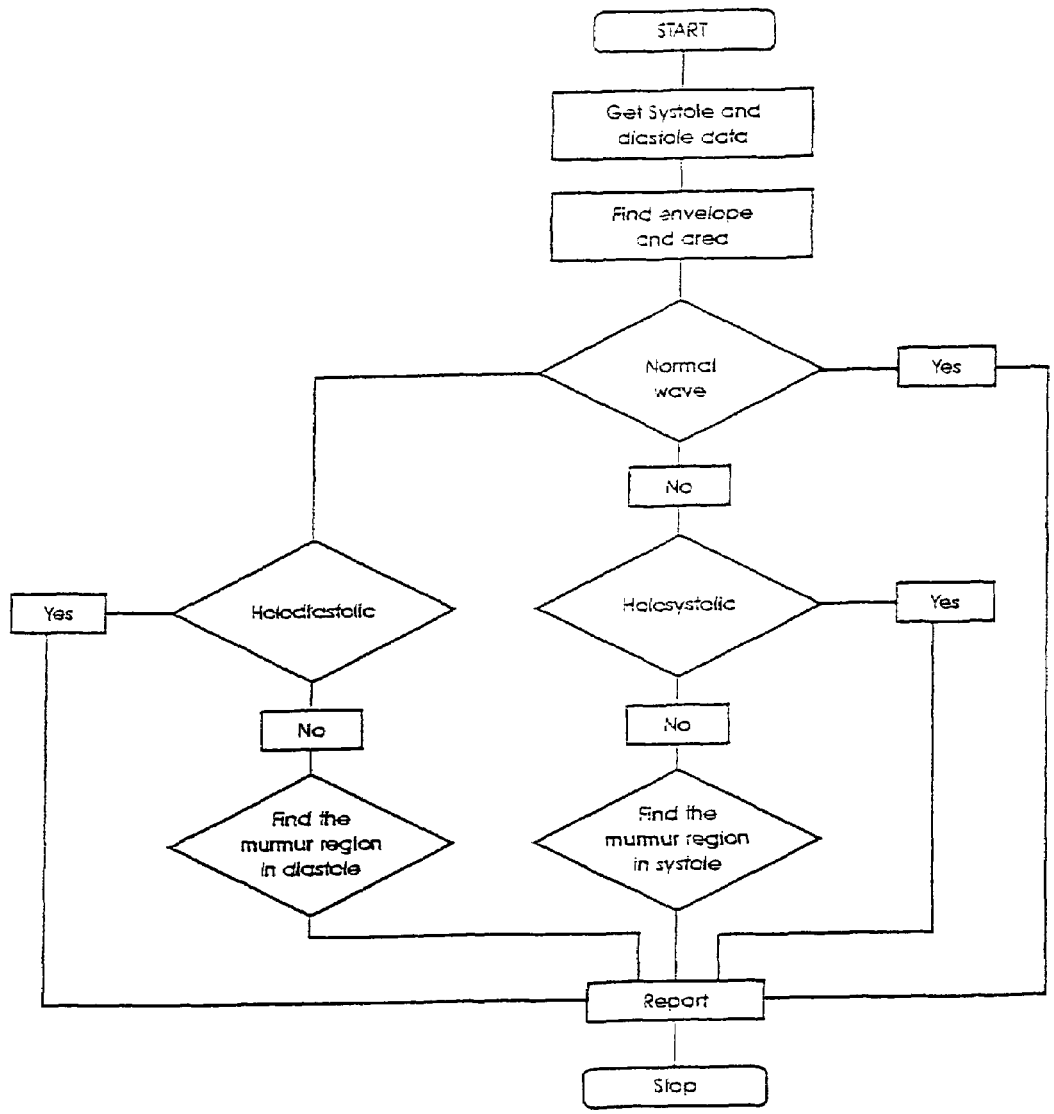
FIG. 19 is a flow diagram summarizing the procedure for detecting murmurs employed by the system of the preferred embodiment.

The systole and diastole data is analyzed after the extraction of S1 and S2 heart sounds from the sound signal. The procedure for detecting murmurs is summarized in the flow diagram shown in FIG. 19.

Figure 20:
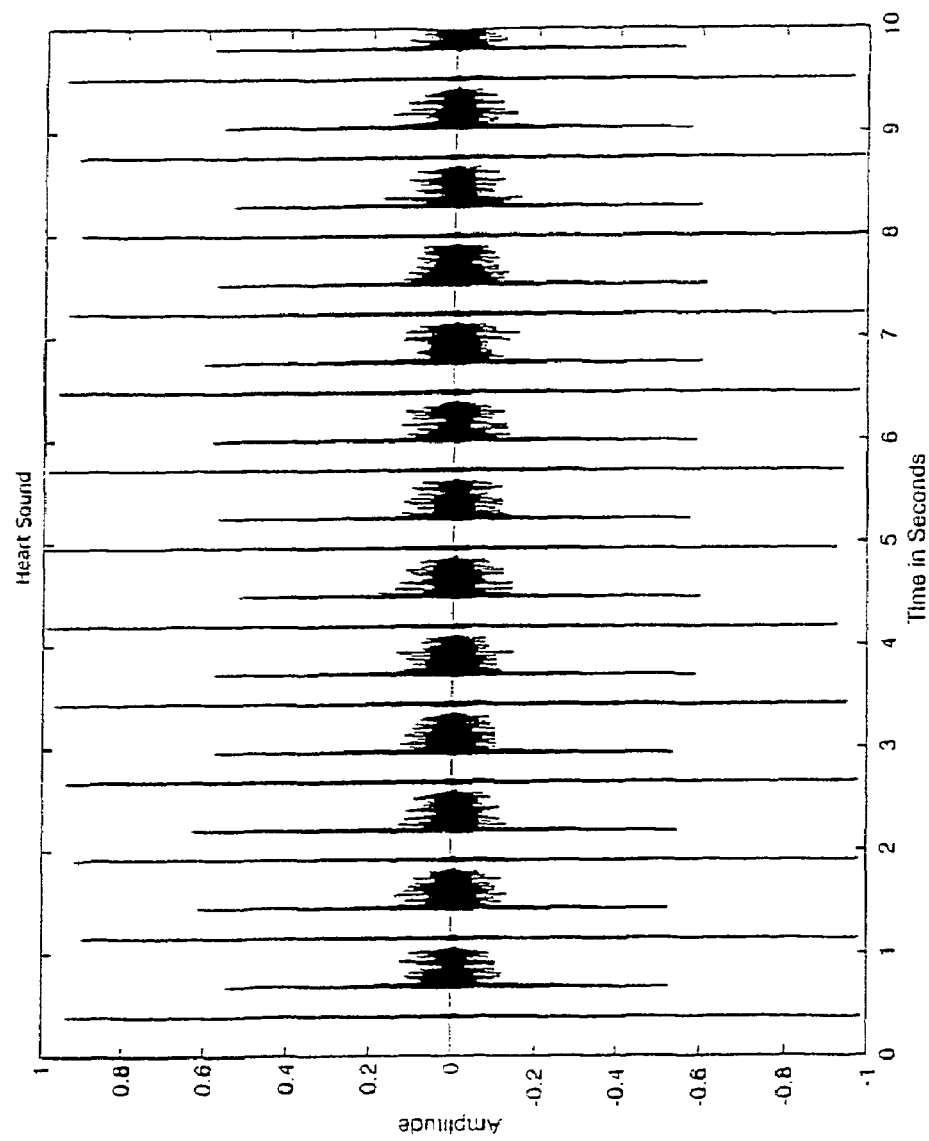
FIG. 20 is a plot of the heart signal, which includes S1, S2, systole and diastole, before extraction of S1 and S2.
Figure 21:
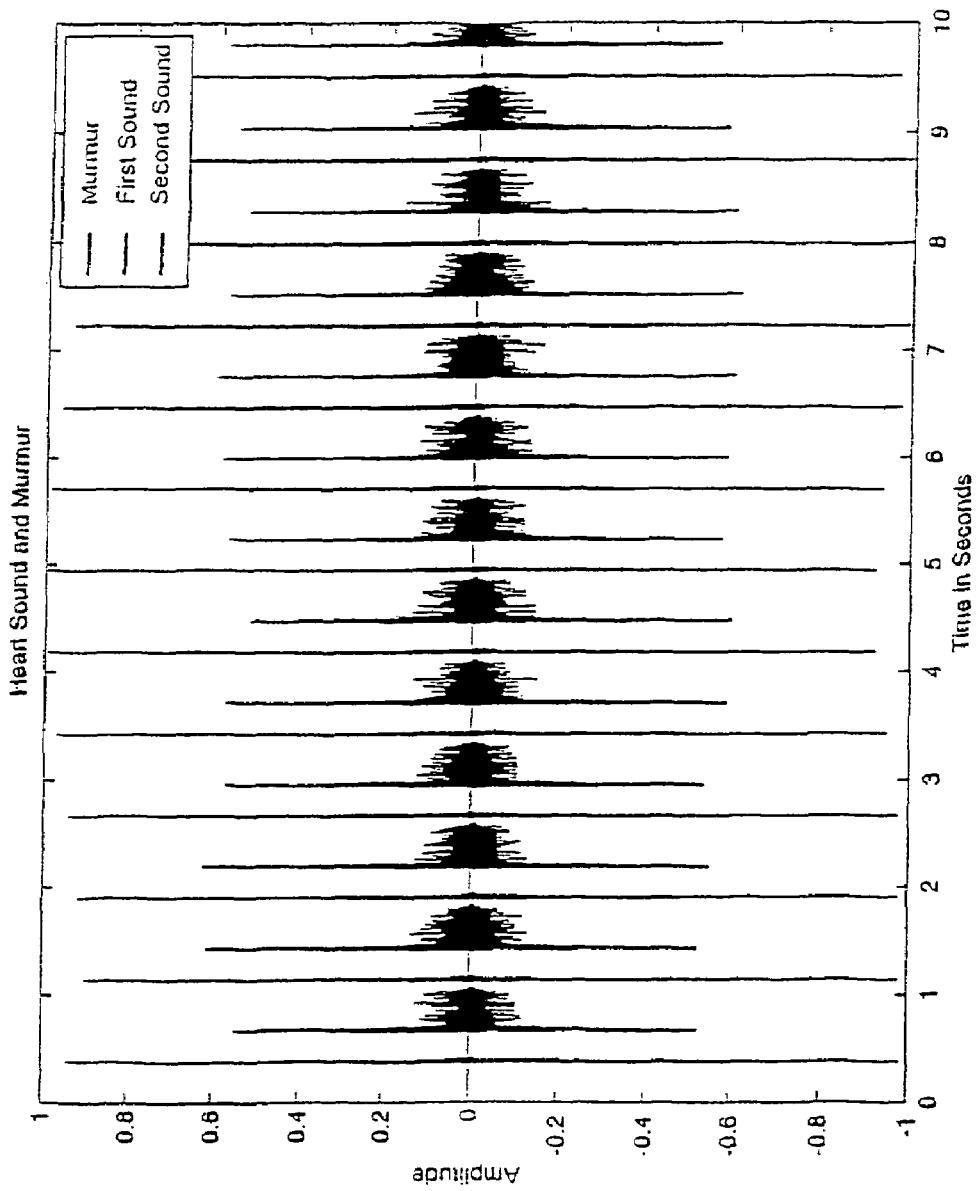
FIG. 21 is a plot of the signal of FIG. 20 after the extraction of S1 and S2 by means of the system of the preferred embodiment.
Figure 22:
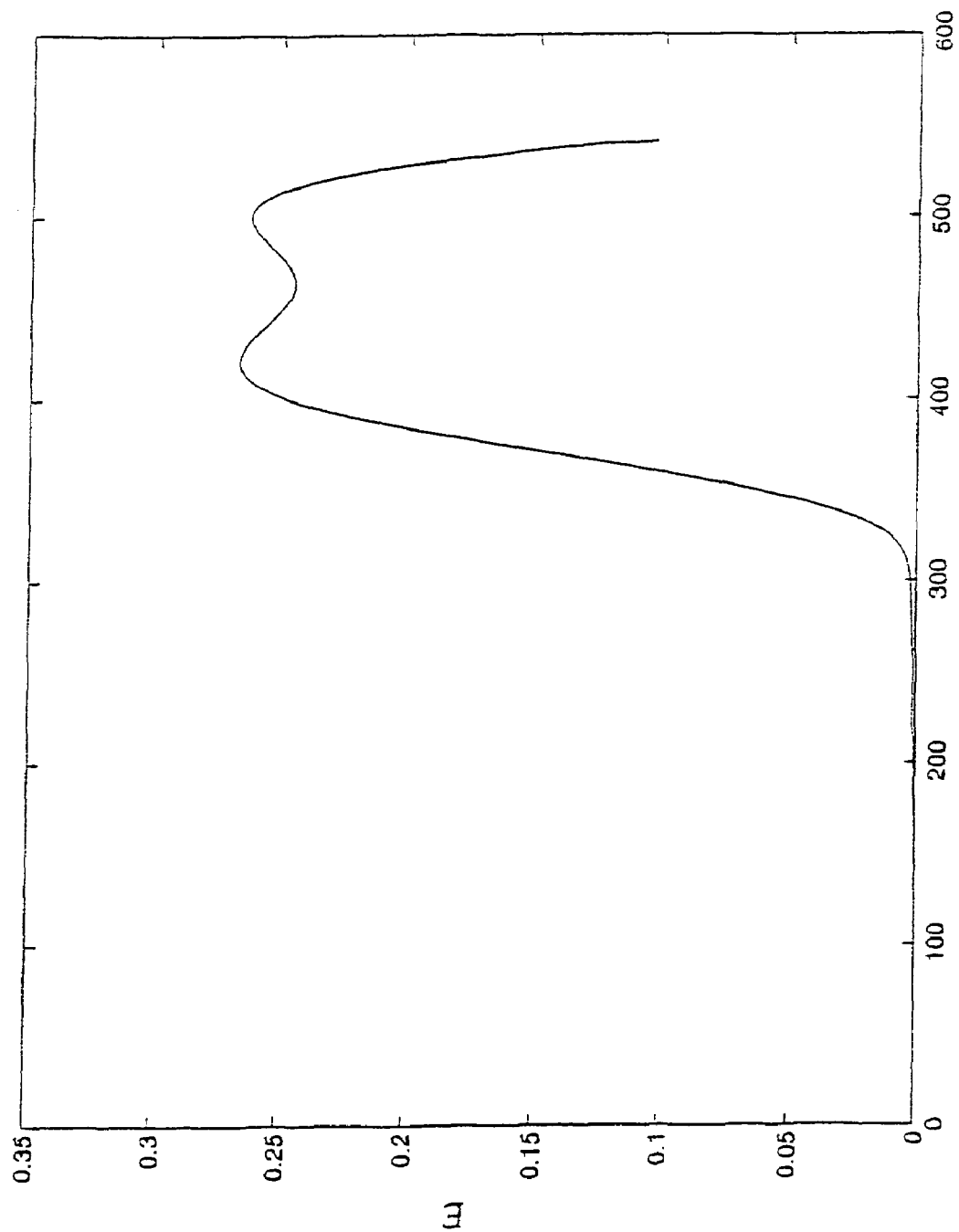
FIG. 22 is a plot of the energy envelope of the early diastole, extracted with the system of the preferred embodiment.

FIG. 20 is a plot of the signal, which includes S1, S2, systole and diastole. The signal after the extraction of S1 and S2 is shown in FIG. 21, in which S1 is visible as the peaks of greatest amplitude and S2 of second greatest amplitude; the murmur regions are the broader regions attached to and to the right of the S2 peaks. Next, the systole and diastole are divided into three regions each. The Shannon's energy envelope is taken for systole and diastole region to reduce the noise and enhance the signal by removing the redundant and unwanted data. A moving average smoothing operation is performed to smooth the envelope. In FIG. 21, the diastole region shows the presence of murmur. The envelope of the early diastole is shown in FIG. 22, plotted as energy E versus time t(s).

The areas of the six regions are then found, after which the ratios of the systole and diastole areas region are determined. The following analysis is performed using both the areas and ratio of the areas.

A ten bit matrix is prepared to indicate the presence of murmurs:

| | |
|---|---|
| First bit | presence of systole murmur |
| Second bit | presence of holosystolic murmur |
| Third bit | presence of systole murmur in early region |
| Fourth bit | presence of systole murmur in middle region |
| Fifth bit | presence of systole murmur in late region |
| Sixth bit | presence of diastolic murmur |
| Seventh bit | presence of holodiastolic murmur |
| Eighth bit | presence of diastole murmur in early region |
| Ninth bit | presence of diastole murmur in middle region |
| Tenth bit | presence of diastole murmur in late region |

If the areas of the regions are below a predefined threshold, a normal wave is diagnosed.

The signal data is first analyzed for murmurs in systolic regions. If the areas of the systole regions are comparable and above a pre defined then holosystolic murmur is detected. If the areas are not comparable then we analyze for the presence of murmurs in each region.

The systole region is divided further into three regions. Area and power spectrum density are considered to detect the presence of murmur in these regions. The area ratio factor of the adjoining regions is also considered to detect the occurrence of murmur. Corresponding bits in the matrix are set when the murmur is detected, by comparing area and power spectrum density with the predefined thresholds. The same process is repeated for diastole region also. Finally the ten bit matrix contains the regions where murmurs are present.

Figure 23:
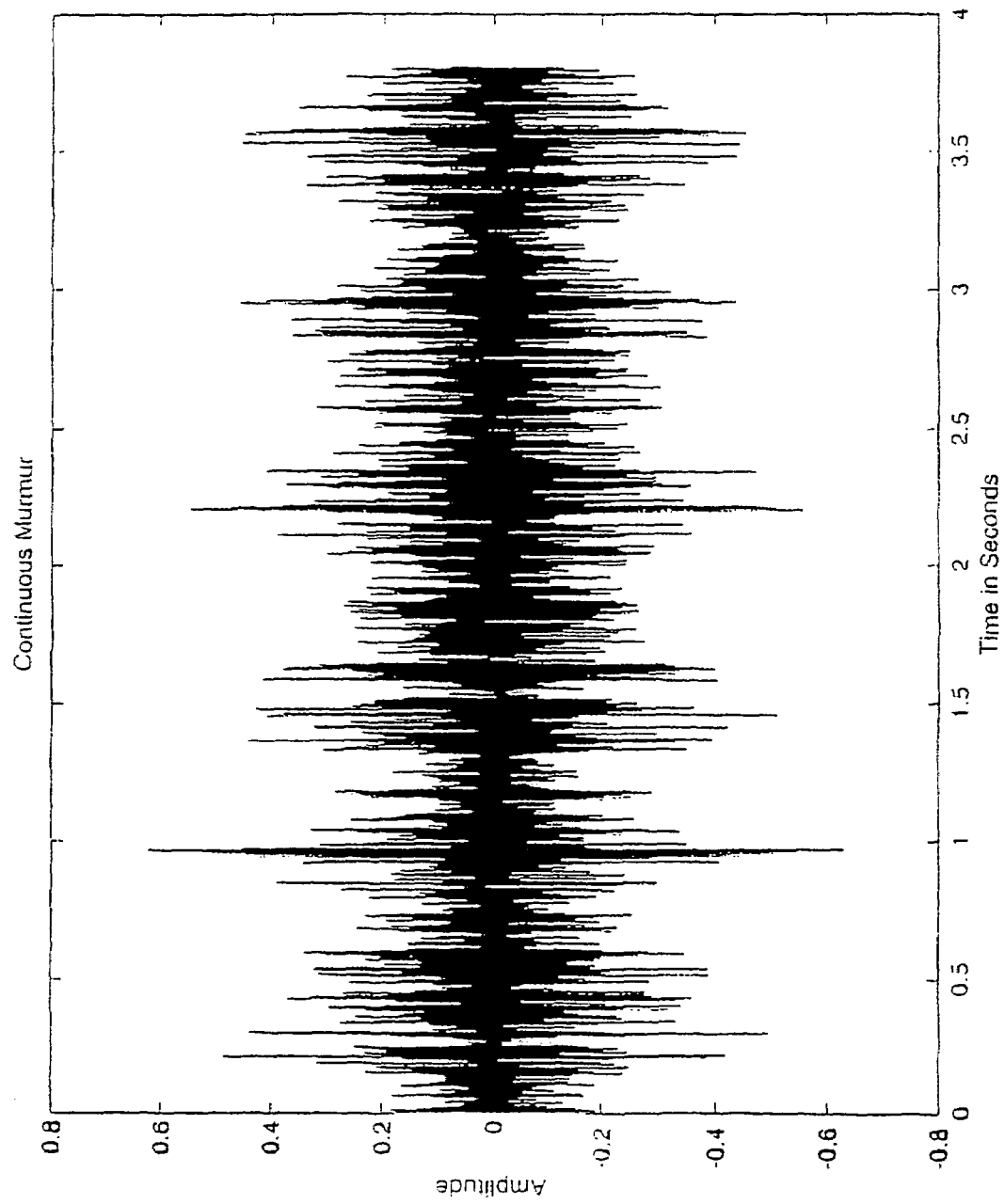
FIG. 23 is a plot of a heart sound signal exhibiting continuous murmur.
Figure 24:
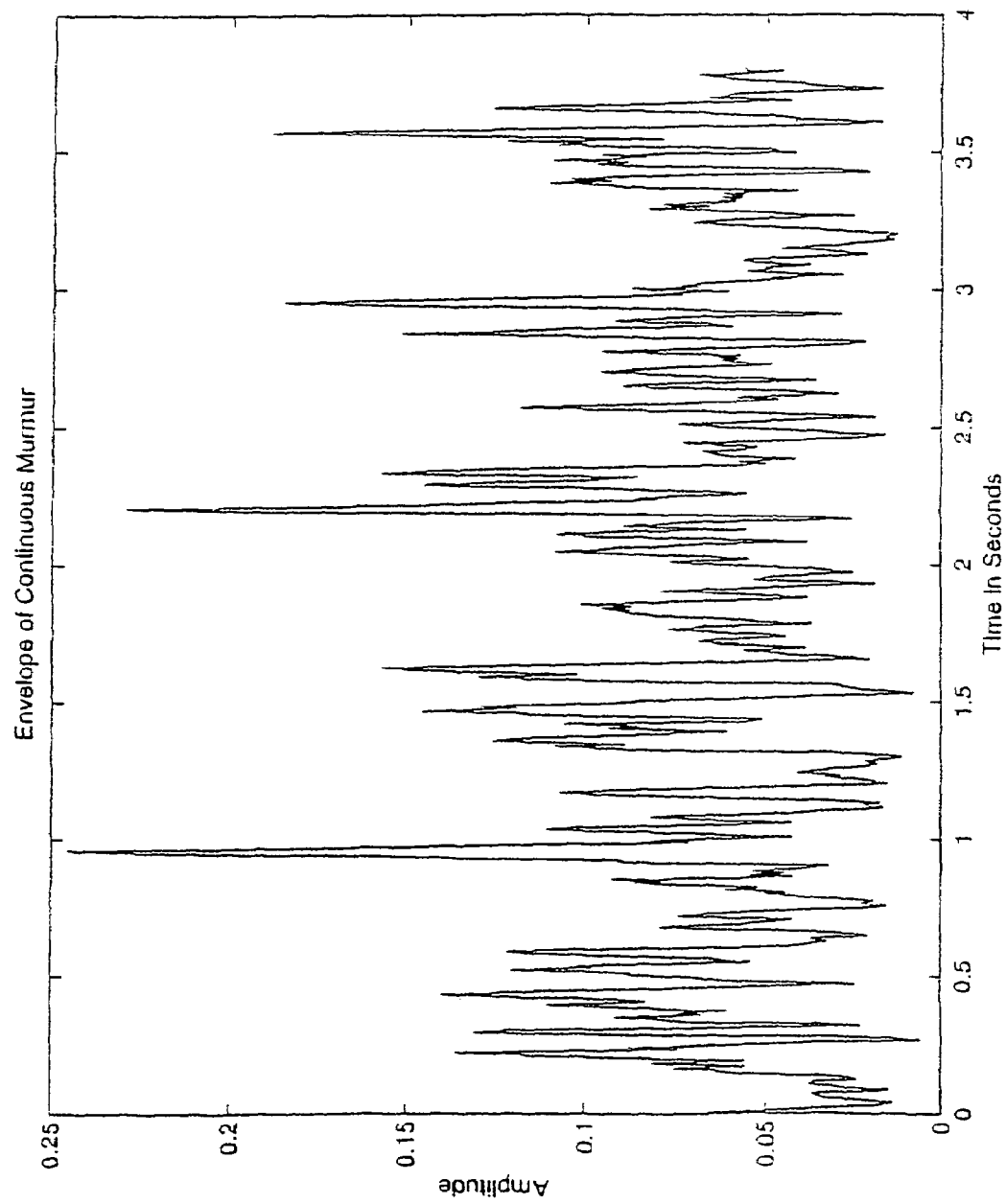
FIG. 24 is a plot of the signal of FIG. 23 following the calculation and smoothing of its Shannon's energy envelope.

Continuous murmur is one of the more serious heart defects. A murmur which is of appreciable amplitude over a period of time and is both holosystolic and holodiastolic is called as continuous murmurs. Continuous murmur (illustrated in the signal plotted as amplitude versus time (s) in FIG. 23) is detected by considering the murmur areas of the entire waveform. The envelope (or energy) of the entire wave is taken using the Shannon's envelope function ($=x^2 \log(x^2)$), which is taken to reduce the noise and enhance the signal by removing the redundant and unwanted data. A moving average is determined to smooth the envelope, and the envelope of the signal is plotted (see FIG. 24).

The area of the envelope is found by dividing it from 20 regions and then decrementing it by 2 up to 10; there are 5 bits which will be set for 20, 18, 16, 14, 12 area region, which forms a bit array. Two parameters (the signal and the number of regions (n) the signal has to be divided into) are used, and an area array containing areas which are n in number are obtained. If the areas returned are appreciable, if they satisfy a threshold and if all the areas returned are almost similar then the particular bit corresponding to the n value is set. If the number of bits set in the bit array is more than 3 then it is a continuous murmur.

Splits are crucial in determining certain diseases. A split may be present both in S1 and S2, and is said to be present in either S1 or S2 when two sounds are heard in that respective sound. In signal processing terms, when there are two appreciable peaks present in the S1 or S2 regions it is said to be split.

The analysis of splits can be summarized as comprising the following steps:

a) get split region;

b) find envelope of split region;

c) find peaks;

d) find maximum peak;

e) separate peaks less than 0.6 of maximum peak;

f) if one or more peaks are thereby identified and split conditions prevail, a split has been found.

Figure 25:
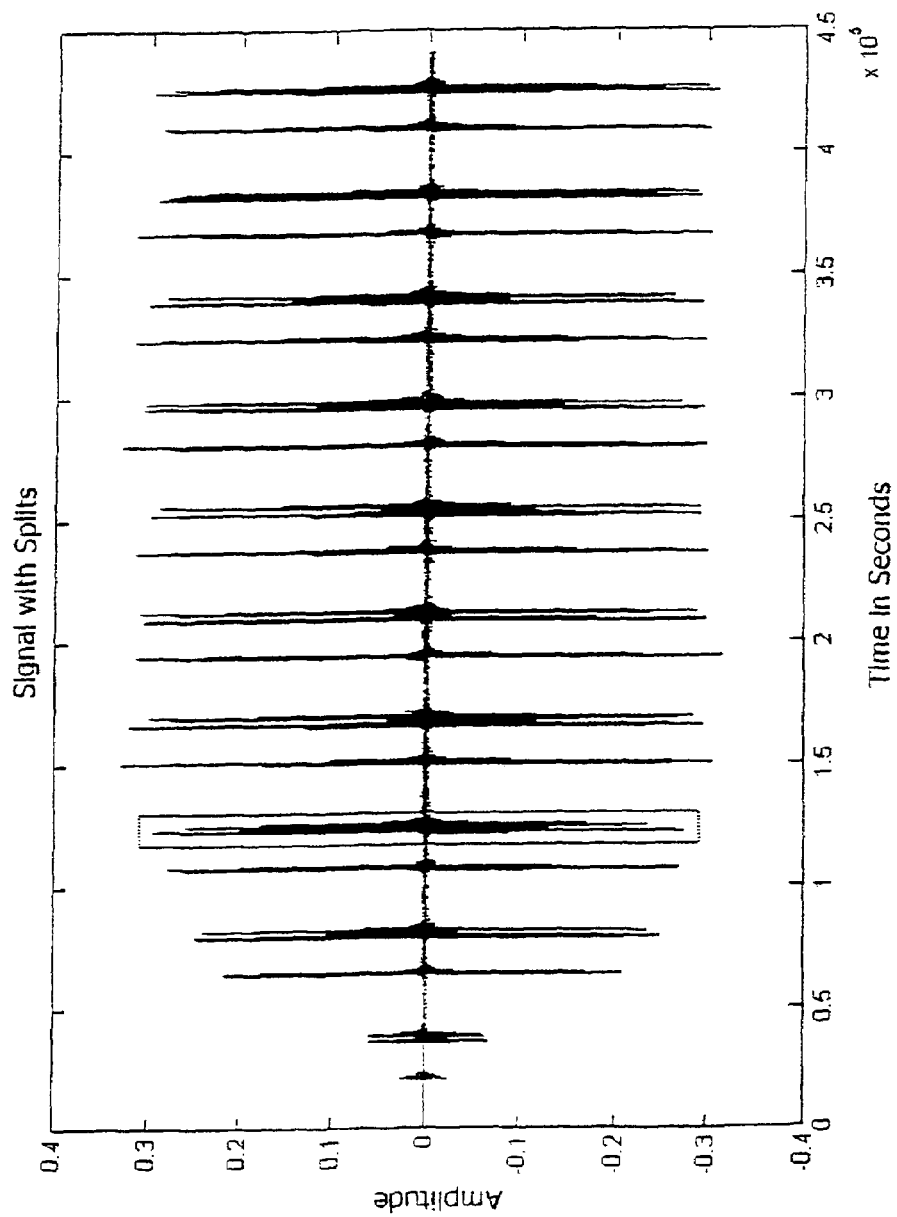
FIG. 25 is a plot of a heart signal waveform exhibiting splits.

A waveform with splits is plotted in FIG. 25 as amplitude versus time (s).

Figure 26:
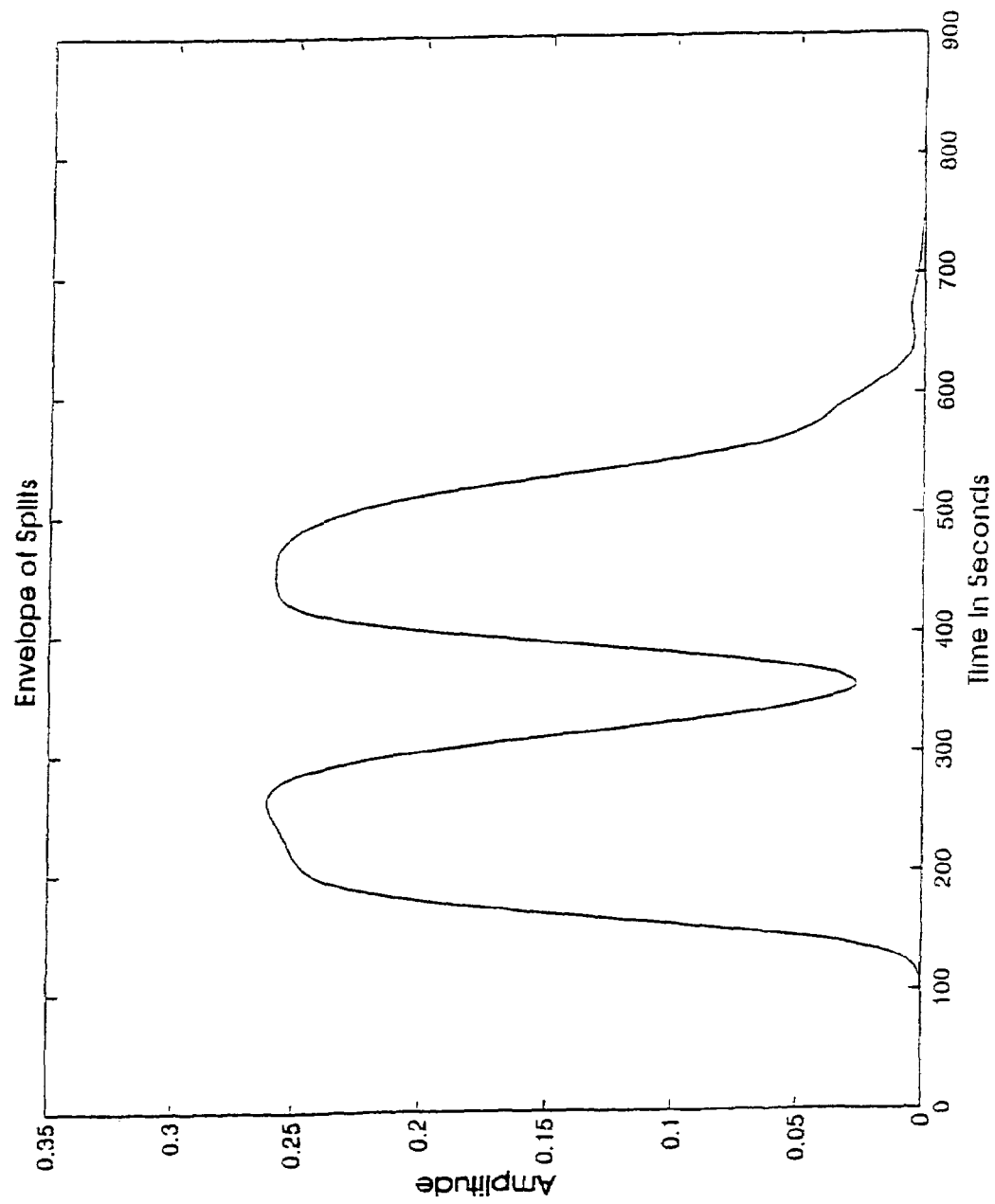
FIG. 26 is a plot of the signal of FIG. 25 following the calculation and smoothing of its Shannon's energy envelope.

The envelope of the region selected as S1 or S2 is then obtained. The Shannon's energy envelope is determined for the systole and diastole regions to reduce the noise and enhance the signal by removing the redundant and unwanted data. The envelope is again $x^2 \log(x^2)$ and is plotted as amplitude versus time (s) in FIG. 26, which shows the envelope of the split region.

The first and second derivatives are used to detect the presence of peaks. The peaks are detected and the maximum peak among them is found. Peaks which are within a predefined threshold of the maximum peak are detected. Peak locations and peak amplitudes are sorted, and the distances between peaks are considered; if these are consistent with the presence of peaks, and if the depth factor criterion is also satisfied, then split is diagnosed. The time interval of split is then calculated.

The following information is used to classify the heart sounds:

1. Nature of the first and second heart sounds;

2. Presence of any other extra heart sounds; and

3. Characteristics of Murmur (if present).

From the first two points it is possible to say whether the heart sound is normal because the absence of any extra heart sounds and the presence of normal first and second heart sounds indicate a normal heart. A murmur may indicate a pathological condition, though it may be innocent.

To determine whether the murmur is innocent or not, the following data is collected:

1. Position of Murmur in the cardiac cycle;

2. Location of Murmur;

3. Nature of Murmur;

4. Frequency of Murmur;

5. Shape of Murmur;

6. Presence of Ejection click;

7. Presence of Opening Snap or Tumor Plops; and

8. Splitting of Heart sounds.

Figure 27:
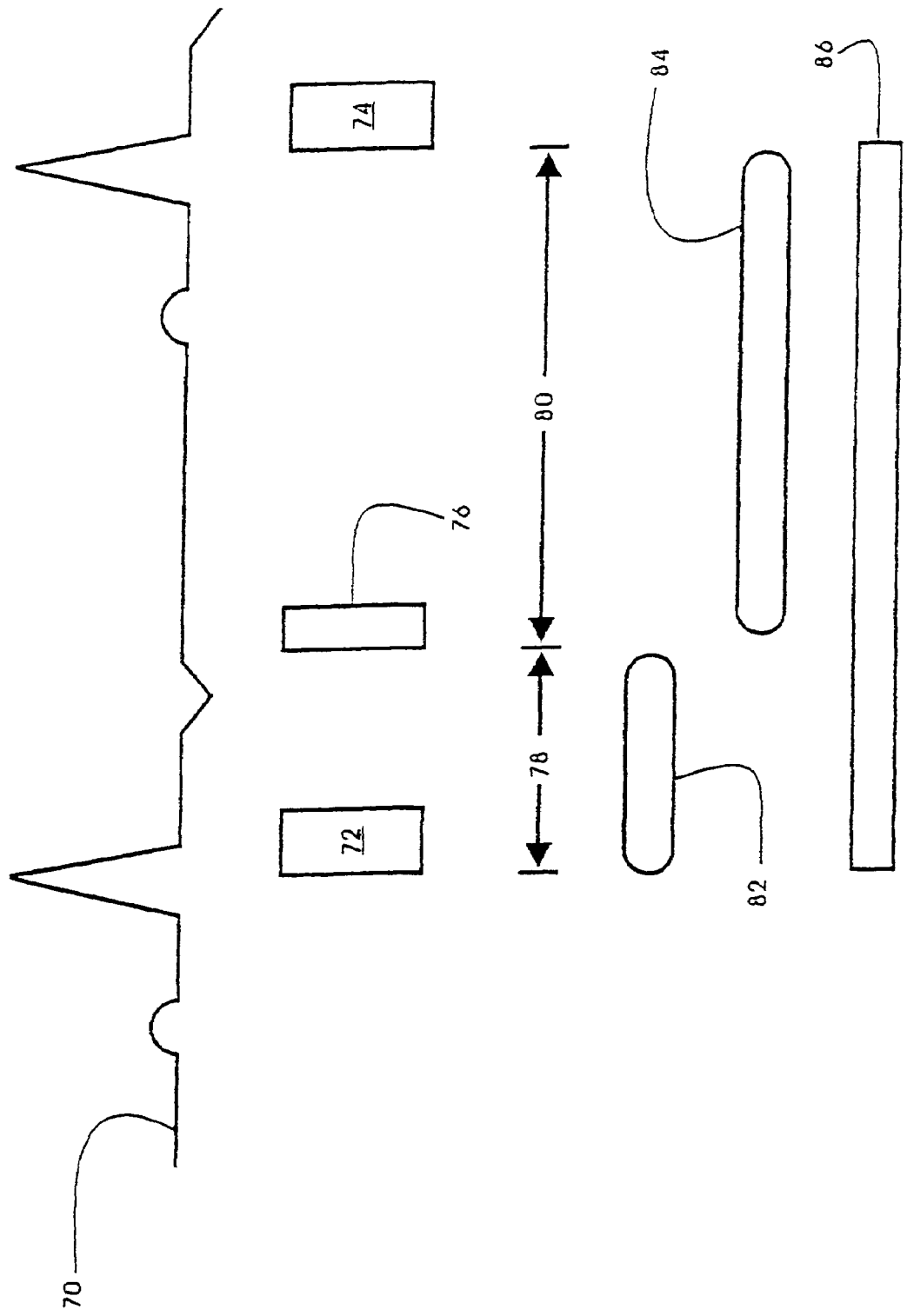
FIG. 27 is a schematic representation of murmur relative to other portions of the heart cycle.

This definition of murmur is illustrated schematically relative to other portions of the heart cycle in FIG. 27. Referring to this figure, an schematic representation of an electrocardiogram 70 is shown with two first heart sounds 72 and 74 and one second heart sound 76. The systole thus corresponds to the interval 78 (from the beginning of first heart sound 72 to the beginning of second heart sound 76), the diastole to the interval 80 (from the beginning of second heart sound 76 to the beginning of the next first heart sound 74). A systolic murmur 82 will therefore be found in the systole interval 78, a diastolic murmur 84 will therefore be found in the diastole interval 80. A continuous murmur 86 will appear in both the systole interval 78 and the diastole interval 80.

The above information is usually found automatically by the analysis program of the system, but in some cases this may not be possible in which case further information is obtained by the medical practitioner or other person performing the examination. The collected information is shown in Table 3.

TABLE 3

| Bit No. | Matrix Parameters Parameter |
| --- | --- |
| 1 | Continuous murmur |
| 2 | Murmur in Systole |
| 3 | Holosystolic murmur |
| 4 | Early systolic murmur |
| 5 | Mid systolic murmur |
| 6 | Late systolic murmur |
| 7 | Split in S1 |
| 8 | Ejection Click |
| 9 | Shape of murmur in systole |
| 10 | High frequency murmur in systole |
| 11 | Murmur in diastole |
| 12 | Holodiastolic murmur |
| 13 | Early diastolic murmur |
| 14 | Mid diastolic murmur |
| 15 | Late diastolic murmur |
| 16 | Split in S2 |
| 17 | Opening snap |
| 18 | Shape of murmur in diastole |
| 19 | High frequency murmur in diastole |
| 20 | Nature of murmur in systole |
| 21 | Nature of murmur in diastole |
| 22 | Nature of continuous murmur |

By using the above information it is possible to categorize the heart sounds into one of the following categories:

1. Normal Heart sound without extra heart sounds;

2. Normal Heart sound with extra heart sounds; and

3. Abnormal or pathological extra sounds.

Based on the above information, each disease is given a weight indicative of the probability of that disease's occurrence.

If a continuous murmur is present, then Atrial Septal Defect, Ventricular Septal Defect, Venous Hum and Patent Ductus Arteriosis are given a high weight. The system queries the examiner on the presence of extra sounds (such as ejection click or opening snap) and the nature of the continuous murmur (i.e. whether it is machinery-like, blowing, harsh or soft).

If the nature of murmur is blowing, then Mitral Regurgitation, Tricuspid Regurgitation, Aortic Stenosis, Pulmonary Stenosis, Aortic Regurgitation, Pulmonary Regurgitation and Ventricular Septal Defect are given a high weight. If the nature of murmur is machinery-like in sound, Patent Ductus Arteriosis and Venous Hum are given a high weight.

If the murmur is not of continuous type, then the heart sound is checked for presence of murmur in systole. If the murmur is holosystolic, Mitral Regurgitation, Tricuspid Regurgitation and Ventricular Septal Defect are given a high weight. If the murmur is early systolic in period, Mitral Regurgitation, Tricuspid Regurgitation and Venous Hum are given a high weight with innocent and pathological murmur having equal weight. If the murmur is present in mid systolic region, then Aortic Stenosis, Pulmonary Stenosis, Atrial Septal Defect, Venous Hum and Mitral Valve Prolapse are given a high weight. If the murmur is present in late systolic period Mitral Regurgitation, Tricuspid Regurgitation, Aortic Stenosis, Pulmonary Stenosis and Mitral Valve Prolapse are given a high weight.

If the murmur extends from early to mid systolic period (approximately first ⅔ of the systole) Mitral Regurgitation, Tricuspid Regurgitation, Aortic Stenosis, Pulmonary Stenosis, Atrial Septal Defect and Ventricular Septal Defect are given a high weight.

If the murmur extends from mid to late systolic period, then Aortic Stenosis, Pulmonary Stenosis, Mitral Valve Prolapse and Atrial Septal Defect are given a high weight. If the murmur is present in early and late period of systole Mitral Regurgitation and Mitral Valve Prolapse are given a high weight. If the murmur is present in early, mid and late period of systole, Aortic Stenosis, Pulmonary Stenosis and Atrial Septal Defect are given a high weight.

If the murmur is present in diastole, then first it is checked for holodiastolic murmur. If the murmur is holodiastolic, Atrial Septal Defect, Ventricular Septal Defect, Patent Ductus Arteriosis and Venous Hum are given a high weight. If the murmur is present in early diastolic period, Aortic Regurgitation, Pulmonary Regurgitation, Mitral Stenosis and Tricuspid Stenosis are given a high weight. If the murmur is present in the mid diastolic period then, Aortic Regurgitation, Pulmonary Regurgitation, Mitral Stenosis, Ventricular Septal Defect and Tricuspid Stenosis are given the highest weight. If the murmur is present in late diastolic period, Mitral Stenosis and Tricuspid Stenosis are given a high weight. If the murmur extends from early to mid diastolic period then, Aortic Regurgitation, Pulmonary Regurgitation, Mitral Stenosis and Tricuspid Stenosis are given a high weight. If the murmur extends from mid diastolic period to late diastolic period, Aortic Regurgitation, Pulmonary Regurgitation, Mitral Stenosis, Tricuspid Stenosis, Atrial Septal Defect and Ventricular Septal Defect are given a high weight. If the murmur is present in early and later period of diastole Aortic Regurgitation, Pulmonary Regurgitation, Mitral Stenosis and Tricuspid Stenosis are given equal weight. If the murmur is present in early, mid and later period of diastole, Mitral Stenosis, Patent Ductus Arteriosis and Venous Hum are given a high weight.

If the murmur is present both in systole and diastole, diseases of systolic and diastolic origin are displayed in bar chart. The system queries the examiner for the following information:

1. Whether ejection click, opening snap, S3 or S4 are present;

2. What shape the murmur has: crescendo, decrescendo, plateau or star shaped; and 3. What nature the sound in systole and diastole assume.

If the murmur is plateau shaped, Mitral Regurgitation, Tricuspid Regurgitation and Ventricular Septal Defect are given a high weight. If the murmur is star shaped, Aortic Stenosis, Pulmonary Stenosis and Atrial Septal Defect are given a high weight. If the murmur is crescendo shaped, Mitral Stenosis and Tricuspid Stenosis are given a high weight. If the shape of the murmur is decrescendo, then Aortic Regurgitation, Pulmonary Regurgitation are given a high weight.

If ejection click is present, Aortic Stenosis and Mitral Valve Prolapse are given a high weight. If opening snap is present, Mitral Stenosis and Tricuspid Stenosis are given a high weight and pathological murmur value is high.

Once the signal has been transmitted to the computer and while—or after—the signal analysis has been performed, several data displays and control windows can be displayed. These can be done either on the computer's screen, or on the screen of a dedicated module provided as a part of the system and having—together with the screen—the required controls for controlling the user controllable functions of the system.

A first screen displays the heart signals as acquired from the data collection device through the serial port. The signal is acquired for 10 seconds and then the software of the system prompts the user with a 'save' dialog box. The acquired data can be saved as .wav, .au and .mat file formats.

This screen thus handles:

1. Reading Heart sound data from the hardware device through serial port;

2. Plotting the signal dynamically during the process of acquiring;

3. Recording the data for 10 seconds; and

4. Saving the acquired data in any of the following three file formats .wav .au or .mat file.

The following software buttons are provided in this first screen:

1) Device: acquires Heart signals from the device through serial port;

2) Disk; for selecting heart sounds from the local hard disk;

3) Acquire; for starting the recording process of heart signals for 10 seconds;

4) Save: appears after the signal acquired for 10 seconds;

5) Exit: for exiting the current application.

A "Automatic Extraction of S1, S2 and murmurs" screen explains the classification of heart sounds (S1, S2, murmur, systole, diastole, etc), and to display separately the three major signals (viz. the original signal, the extracted and highlighted systole and diastole regions including murmur, and the and highlighted S1 and S2 regions).

This and all other screens include the following function buttons:

1) Extract Manually: to go to manual extraction screen;

2) Proceed with Diagnosis: to go to diagnosis report screen;

3) Disk: to select heart sounds from the local hard disk;

4) Device: to acquire heart signals from the device through the serial port;

5) Exit: to exit the current application;

and the following controls:

1) Play: to play the heart sound;

2) Stop: to stops the heart sound;

3) Pause: to pause the heart sound;

4) Rewind: to rewind the heart sound;

5) Zoom in: to zoom in to the selected region in the signal;

6) Zoom out: to zoom out the selected region in the signal; and

7) File Archive: to select heart sounds by opening the file dialog box.

The diagnosis screen is provided for displaying the diagnosis and to prompt for the examiner's suggestion concerning opening snap or ejection click (as described above). The examiner selects, for each of "opening snap" and "ejection click", one of "yes", "no" or "doubtful" by means of radio buttons (i.e. where only one selection can be made from any group of options).

This screen also presents a "View Diagnosis" button, which takes the user to a pie bar representation screen.

The pie bar representation screen displays the disease details in chart format. It has two types of charts, Pie and Bar charts, and a "Differential diagnosis" button to transfer to the Differential diagnosis screen and check for the presence of murmur.

The Pie Chart is used to display the main categories of heart disease, innocent murmur and pathological murmur. The Bar Chart is used to display the disease possibility ratios in bar chart format. For example:

MVP 30%
PDA 40% means that the diagnosed signal indicates that there is a 30% chance that the patient has mitral valve prolapsed and a 40% chance that the patient has patent Ductus arterioles.

When Differential Diagnosis button is pressed, the following conditions are checked:

1) If murmur is present in both systole and diastole period, then the flow moves from pie/bar screen to systole screen and then moves to diastole screen;

2) If continuous murmur is present in the heart sound, the user is transferred to the continuous screen;

3) If murmur is present in systole period, flow will move from pie/bar screen to the systole screen;

4) If murmur is present only in the diastole period, flow moves from the pie/bar screen to the diastole screen.

The Manual Extraction screen is used to select S1, S2 and the murmur region manually from a complete selected cycle. If the extraction algorithm fails, control is automatically transferred to the manual extraction screen, or the user can explicitly select manual extraction screen if algorithm appears to be insufficient.

This screen contains the following buttons:

1) 'Select Cycle': to select or remove one complete heart sound cycle;

2) 'Select S1': to select or remove S1 period from full cycle;

3) 'Select S2': to select or remove S2 period from full cycle;

4) 'Confirm Selection': To confirm the selected region and to proceeds for murmur analysis;

5) 'Cancel'.

The following procedures are used to select S1, S2 and murmurs:

1) Press 'Select Cycle' button, then select one complete heart sound cycle from signal.

2) Press 'Select S2' button, then select S1 heart sound from selected cycle region.

3) Press 'Select S2' button, then select S2 heart sound from selected cycle region.

4) Finally press 'Confirm Selection' button.

The Systole screen is displayed if a murmur is present in the systole period. It displays the full signal and also provides an option to the examiner in the form of a questionnaire, which enables the examiner to choose what he or she observes from the heart sound when prompted for "What do you observe from the SYSTOLIC murmur?" Here the examiner can select from the provided radio buttons the nature of the sound and the shape of the murmur that he has observed. The nature of the sound has the following options:

a) Machinery
b) Blowing
c) Harsh
d) Mild

The examiner can listen to sample sounds of each type by pressing sample sound symbol buttons. The shape of the murmur has the following options:

a) Crescendo
b) Decrescendo
c) Plateau
d) Star

This screen also contains a "Next?" button, for selecting to proceed with for further analysis.

The Differential diagnosis "Continuous" screen is displayed if the murmur is continuously present. It also provides options to the doctor in the form of questionnaire. This enables the examiner to choose what is observed from the sounds. The examiner is asked "What do you observe from the CONTINUOUS murmur?" The examiner selects radio buttons provided about the "nature of the sound" as described above.

This screen also contains the following buttons:

1) "Next?": pressed for further analysis;

2) "Back?": for the previous screen.

The "Diastole" screen is displayed if the murmur is present in the diastole period. It displays the full signal and also provides an option to the examiner in the form of questionnaire asking "What do you observe from the DIASTOLIC murmur?" The examiner can again select from radio buttons concerning "nature of the sound?" and the "shape of the murmur."

This screen also contains the "Next?" and "Back?" buttons.

The Differential Diagnosis screen also contains a description of the murmur, and if murmur is present in the systole, it will display the occurrence of the murmur and its timing, shape and nature.

If murmur is present in the diastole, this screen indicates the occurrence of the murmur, and provides its timing, shape and nature. If the murmur is continuous, its amplitude will be appreciable and the murmur prolonged throughout the wave. This screen contains a bar chart on the different diseases probabilities and a "Defect Details" button; if the button is pressed it will proceed to the "Defect Details" screen.

The Defect Details screen contains a pop-up menu that lists various diseases. If the examiner selects a disease from pop-up menu, information about that disease is be displayed. This screen also includes a "BACK" button to return to the previous screen.

The "Normal" screen provides information about the normal heart sound. It displays a pie chart with 1% Abnormal and 99% Normal.

Modifications within the spirit and scope of the invention may be readily effected by those skilled in the art. It is to be understood, therefore, that this invention is not limited to the particular embodiments described by way of example hereinabove.

I claim:

1. A method of analysing a heart signal from a beating heart comprising:
    collecting said heart signal; with a heart diagnosis system; and analyzing said heart signal with said heart diagnosis system by:

identifying peaks within said heart signal, wherein the peaks are regions where the amplitude of said heart signal is higher than a predetermined level;

calculating characteristic parameters of the peaks;

clustering the peaks based on at least one of the calculated characteristic parameters of the peaks;

eliminating any false peaks of said peaks due to artifacts and breathing sounds;

identifying first heart sounds and second heart sounds based on the clusters of the peaks, and then identifying systoles and diastoles, wherein the identification of first heart sounds, second heart sounds, systoles and diastoles does not need external timing reference;

dividing each of the identified systoles and diastoles into a plurality of regions and then determining an energy envelope for each of the plurality of regions; and determining an area for each of said energy envelopes;

and classifying said heart signal by an analysis incorporating at least said areas.

2. A method as claimed in claim 1, wherein the analysis incorporating at least said areas comprises a step of comparing one or more of said areas with at least one other of said areas.

3. A method as claimed in claim 2, wherein the comparing of one or more of said areas with at least one other of said areas comprises steps of:

determining one or more ratios, each comprising the ratio of one of said areas and another of said areas, and comparing said ratios with respective predetermined threshold values for said ratios, and thereby determining one or more characteristics of said heart signal.

4. A method as claimed in claim 2, wherein the comparing of one or more of said areas with at least one other of said areas comprises steps of:

comparing one or more of said areas with respective predetermined threshold values for said areas, and thereby determining one or more characteristics of said heart signal.

5. A method as claimed in claim 1, further comprising step of: smoothing each of said energy envelopes.

6. A method as claimed in claim 1, wherein each of said energy envelopes is a Shannon's energy envelope.

7. A method as claimed in claim 1, wherein the step of determining the energy envelope comprises determining the energy envelope for the systolic region and for the diastolic region.

8. A method as claimed in claim 1, wherein the step of determining the energy envelope comprises determining the energy envelope for a plurality of regions within each of the systolic and diastolic regions.

9. A method as claimed in claim 1, wherein the step of determining the energy envelope comprises determining the energy envelope for at least three regions within the systolic region and for at least three regions within the diastolic region.

10. A method as claimed in claim 1, wherein said heart signal is a sound signal.

11. A method as claimed in claim 1, further comprising step of prompting a user for user input if unable to form a diagnosis, said user input including a user interpretation of said heart signal.

12. A method as claimed in claim 1, wherein the classifying of said heart signal includes detecting at least one of a systolic murmur, a diastolic murmur and a continuos murmur.

13. A method as claimed in claim 1, wherein the artifacts include motion artifacts.

14. An apparatus for analysing a heart signal from a beating heart, said apparatus comprising:

a detector for collecting said heart signal;

data processing means for:

receiving said heart signal from the detector;

identifying peaks within said heart signal, wherein the peaks are regions where the amplitude of said heart signal is higher than a predetermined level;

calculating characteristic parameters of the peaks;

clustering the peaks based on at least one of the calculated characteristic parameters of the peaks;

eliminating any false peaks of said peaks due to artifacts and breathing sounds;

identifying first heart sounds and second heart sounds based on the clusters of the peaks, and then identifying systoles and diastoles, wherein the identification of first heart sounds, second heart sounds, systoles and diastoles does not need external timing reference;

dividing each of the identified systoles and diastoles into a plurality of regions and then determining an energy envelope for each of the plurality of regions; and determining an area for each of said energy envelopes;

and forming a classification of said signal by an analysis incorporating at least said area; and data output means for displaying said classification.

15. An apparatus as claimed in claim 14, wherein said data processing means is operable to compare one or more of said areas with at least one other of said areas.

16. An apparatus as claimed in claim 14, wherein said data processing means is operable to determine one or more ratios, each comprising the ratio of one of said areas and another of said areas, and to compare said ratios with respective predetermined threshold values for said ratios, and thereby determine one or more characteristics of said heart signal.

17. An apparatus as claimed in claim 14, wherein said data processing means is operable to compare one or more of said areas with respective predetermined threshold values for said areas, and thereby determining one or more characteristics of said heart signal.

18. An apparatus as claimed in claim 14, wherein said data processing means is further operable to smooth each of said energy envelopes.

19. An apparatus as claimed in claim 14, wherein each of said energy envelopes is a Shannon's energy envelope.

20. An apparatus as claimed in claim 14, wherein said data processing means is operable to determine the energy envelope for the systolic region and for diastolic region.

21. An apparatus as claimed in claim 14, wherein said data processing means is operable to determine the energy envelope for a plurality of regions within each of the systolic and diastolic regions.

22. An apparatus as claimed in claim 14, wherein said data processing means is operable to determine the energy envelope for the energy envelope for at least three regions within the systolic region and for at least three regions within the diastolic region.

23. An apparatus as claimed in claim 14, wherein said heart signal is a sound signal.

24. An apparatus as claimed in claim 14, wherein said data processing means further includes means for prompting a user for user input and for receiving use input, and is operable to prompt said user for user input if unable to form a diagnosis, said user input including a user interpretation of said heart signal.

* * * * *